US006482422B1

(12) United States Patent
Paul et al.

(10) Patent No.: US 6,482,422 B1
(45) Date of Patent: *Nov. 19, 2002

(54) ABSORBENT ARTICLE WHICH MAINTAINS OR IMPROVES SKIN HEALTH

(75) Inventors: Susan Carol Paul, Alpharetta, GA (US); Frank Jerrel Akin, Marietta, GA (US); Robert Cosmo Di Luccio, Alpharetta, GA (US); Dennis Stein Everhart, Alpharetta, GA (US); Elizabeth Deibler Gadsby, Marietta, GA (US); Pamela Jean Mayberry, Roswell, GA (US); Audra Stefanik Wright, Woodstock, GA (US); Ali Yahiaoui, Roswell, GA (US); Michael John Faulks, Neenah, WI (US); Duane Gerard Krzysik, Appleton, WI (US); Karen Marie Menard, Neenah, WI (US); David Charles Musil, Appleton, WI (US); Frank Andrew Rosch, III, Sherwood, WI (US); Gordon Allen Shaw, Greenville, WI (US); David John Tyrrell, Appleton, WI (US); Diane Michele Underhill, Neenah, WI (US); Jeffrey Michael Hockersmith, Mill Creek, WA (US); Gunilla Elsa Gillberg-LaForce, Painted Post, NY (US); Wade Bolton May, New Orleans, LA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 37 days.

This patent is subject to a terminal disclaimer.

(21) Appl. No.: 09/671,356

(22) Filed: Sep. 27, 2000

Related U.S. Application Data

(62) Division of application No. 09/379,431, filed on Aug. 23, 1999.

(51) Int. Cl.$^7$ ............ A01N 25/34; A61F 13/15
(52) U.S. Cl. .......... 424/402; 604/360; 604/367; 604/378
(58) Field of Search .......... 424/402; 604/358, 604/367

(56) References Cited

U.S. PATENT DOCUMENTS 3,371,667 A    3/1968    Morse
(List continued on next page.)

FOREIGN PATENT DOCUMENTS

EP    0 343 941 A2    11/1989
(List continued on next page.)

OTHER PUBLICATIONS

American Society for Testing Materials (ASTM) Designation: D 1321–92, "Standard Test Method for Needle Penetration of Petroleum Waxes," pp. 483–485, published Dec. 1992.

(List continued on next page.)

Primary Examiner—Thurman K. Page
Assistant Examiner—Isis Ghali
(74) Attorney, Agent, or Firm—Alyssa A. Dudkowski; Jeffrey B. Curtin

(57) ABSTRACT

An absorbent article includes a vapor permeable backsheet, a liquid permeable topsheet positioned in facing relation with the backsheet; and an absorbent body located between the backsheet and the topsheet. The absorbent body may include multiple zones of high air permeability. The absorbent article may also include a ventilation layer between the absorbent body and the backsheet and a surge management layer between the absorbent body and the topsheet. The article exhibits improved air exchange within the article during use. As a result, the article maintains the temperature and exhibits substantially reduced levels of hydration of the wearer's skin when in use which renders the skin less susceptible to the viability of microorganisms. The absorbent article may further include lotion formulations and/or treatment compositions thereon for maintaining or improving skin health.

21 Claims, 11 Drawing Sheets

U.S. PATENT DOCUMENTS

| | | |
|---|---|---|
| 3,431,911 A | 3/1969 | Meisel, Jr. |
| 3,563,243 A | 2/1971 | Lindquist |
| 3,805,790 A | 4/1974 | Kaczmarzyk et al. |
| 3,889,679 A | 6/1975 | Taylor |
| 3,916,900 A | 11/1975 | Breyer et al. |
| 3,945,386 A | 3/1976 | Anczurowski et al. |
| 4,055,184 A | 10/1977 | Karami |
| 4,100,324 A | 7/1978 | Anderson et al. |
| 4,233,212 A | 11/1980 | Otoi et al. |
| 4,276,338 A | 6/1981 | Ludwa et al. |
| 4,306,559 A | 12/1981 | Nishiwawa et al. |
| 4,389,211 A | 6/1983 | Lenaghan |
| 4,542,199 A | 9/1985 | Kaminsky et al. |
| 4,560,372 A | 12/1985 | Pieniak |
| 4,568,341 A | 2/1986 | Mitchell et al. |
| 4,592,751 A | 6/1986 | Gegelys |
| 4,604,313 A | 8/1986 | McFarland et al. |
| 4,608,292 A | 8/1986 | Lassen |
| 4,624,666 A | 11/1986 | DeRossett et al. |
| 4,634,440 A | 1/1987 | Widlund et al. |
| 4,676,786 A | 6/1987 | Nishino |
| 4,704,112 A | 11/1987 | Suzuki et al. |
| 4,731,065 A | 3/1988 | Yamada |
| 4,781,710 A | 11/1988 | Megison et al. |
| 4,787,896 A | 11/1988 | Houghton et al. |
| 4,798,603 A | 1/1989 | Meyer et al. |
| 4,809,493 A | 3/1989 | Genba et al. |
| 4,839,165 A | 6/1989 | Hoppe et al. |
| 4,839,168 A | 6/1989 | Abe et al. |
| 4,840,692 A | 6/1989 | Kamstrup-Larsen |
| 4,906,460 A | 3/1990 | Kim et al. |
| 4,908,026 A | 3/1990 | Sukiennik et al. |
| 4,990,147 A | 2/1991 | Freeland |
| 5,009,813 A | 4/1991 | Watanabe et al. |
| 5,030,229 A | 7/1991 | Yang |
| 5,061,260 A | 10/1991 | Callahan et al. |
| 5,062,840 A | 11/1991 | Holt et al. |
| 5,064,802 A | 11/1991 | Stevens et al. |
| 5,069,898 A | 12/1991 | Goldberg |
| 5,078,710 A | 1/1992 | Suda et al. |
| 5,137,525 A | 8/1992 | Glassman |
| 5,141,794 A | 8/1992 | Arroyo |
| 5,171,236 A | 12/1992 | Dreier et al. |
| 5,171,238 A | 12/1992 | Kajander |
| 5,176,668 A | 1/1993 | Bernardin |
| 5,176,672 A | 1/1993 | Bruemmer et al. |
| 5,189,192 A | 2/1993 | LaPointe et al. |
| 5,192,277 A | 3/1993 | Chung et al. |
| 5,192,606 A | 3/1993 | Proxmire et al. |
| 5,204,429 A | 4/1993 | Kaminsky et al. |
| 5,263,948 A | 11/1993 | Karami et al. |
| 5,272,236 A | 12/1993 | Lai et al. |
| 5,278,272 A | 1/1994 | Lai et al. |
| 5,294,478 A | 3/1994 | Wanek et al. |
| 5,300,053 A | 4/1994 | Genaro |
| 5,304,161 A | 4/1994 | Noel et al. |
| 5,306,266 A | 4/1994 | Freeland |
| 5,324,278 A | 6/1994 | Visscher et al. |
| 5,349,100 A | 9/1994 | Mintz |
| 5,350,624 A | 9/1994 | Georger et al. |
| 5,352,749 A | 10/1994 | DeChellis et al. |
| 5,356,405 A | 10/1994 | Thompson et al. |
| 5,364,382 A | 11/1994 | Latimer et al. |
| 5,366,451 A | 11/1994 | Levesque |
| 5,366,452 A | 11/1994 | Widlund et al. |
| 5,374,696 A | 12/1994 | Rosen et al. |
| 5,383,870 A | 1/1995 | Takai et al. |
| 5,387,209 A | 2/1995 | Yamamoto et al. |
| 5,391,160 A | 2/1995 | Runeman et al. |
| 5,397,316 A | 3/1995 | LaVon et al. |
| 5,439,458 A | 8/1995 | Noel et al. |
| 5,451,442 A | 9/1995 | Pieniak et al. |
| 5,462,541 A | 10/1995 | Bruemmer et al. |
| 5,482,765 A | 1/1996 | Bradley et al. |
| 5,486,166 A | 1/1996 | Bishop et al. |
| 5,490,846 A | 2/1996 | Ellis et al. |
| 5,505,720 A | 4/1996 | Walters et al. |
| 5,506,915 A | 4/1996 | Hanson et al. |
| 5,514,104 A | 5/1996 | Cole et al. |
| 5,514,105 A | 5/1996 | Goodman, Jr. et al. |
| 5,514,120 A | 5/1996 | Johnston et al. |
| 5,520,674 A | 5/1996 | Lavon et al. |
| 5,533,991 A | 7/1996 | Kirby et al. |
| 5,536,264 A | 7/1996 | Hsueh et al. |
| 5,549,775 A | 8/1996 | Odorzynski |
| 5,558,655 A | 9/1996 | Jezzi et al. |
| 5,558,658 A | 9/1996 | Menard et al. |
| 5,562,650 A | 10/1996 | Everett et al. |
| 5,569,226 A | 10/1996 | Cohen et al. |
| 5,571,096 A | 11/1996 | Dobrin et al. |
| 5,591,148 A | 1/1997 | McFall et al. |
| 5,593,399 A | 1/1997 | Tanzer et al. |
| 5,603,707 A | 2/1997 | Trombetta et al. |
| 5,609,587 A | 3/1997 | Roe |
| 5,611,790 A | 3/1997 | Osborn, III et al. |
| 5,613,962 A | 3/1997 | Kenmochi et al. |
| 5,614,283 A | 3/1997 | Potnis et al. |
| 5,624,422 A | 4/1997 | Allen |
| 5,628,737 A | 5/1997 | Dobrin et al. |
| 5,637,105 A | 6/1997 | Tanaka et al. |
| 5,641,441 A | 6/1997 | Yang |
| 5,643,238 A | 7/1997 | Baker |
| 5,643,239 A | 7/1997 | Bodford et al. |
| 5,643,240 A | 7/1997 | Jackson et al. |
| 5,653,702 A | 8/1997 | Brohammer et al. |
| 5,662,633 A | 9/1997 | Doak et al. |
| 5,662,634 A | 9/1997 | Yamamoto et al. |
| 5,669,895 A | 9/1997 | Murakami et al. |
| 5,669,896 A | 9/1997 | Kielpikowski |
| 5,674,212 A | 10/1997 | Osborn, III et al. |
| 5,674,214 A | 10/1997 | Visscher et al. |
| 5,677,028 A | 10/1997 | Ravella |
| 5,683,375 A | 11/1997 | Osborn, III et al. |
| 5,695,487 A | 12/1997 | Cohen et al. |
| 5,702,382 A | 12/1997 | Osborn, III et al. |
| 5,810,797 A * | 9/1998 | Menard et al. |
| 5,843,056 A | 12/1998 | Good et al. |
| 5,853,402 A | 12/1998 | Faulks et al. |
| 5,871,763 A | 2/1999 | Luu et al. |
| 5,879,341 A | 3/1999 | Odorzynski et al. |
| 5,919,179 A | 7/1999 | Faulks et al. |
| 6,107,537 A * | 8/2000 | Elder et al. |
| 6,120,783 A * | 9/2000 | Roe et al. |
| 6,149,934 A * | 11/2000 | Krzy et al. |
| 6,152,906 A | 11/2000 | Faulks et al. |

FOREIGN PATENT DOCUMENTS

| | | |
|---|---|---|
| EP | 0 774 242 A1 | 5/1997 |
| EP | 0 797 968 A1 | 10/1997 |
| EP | 0 804 914 A1 | 11/1997 |
| EP | 0 813 848 A1 | 12/1997 |
| EP | 0 875 233 A1 | 11/1998 |
| GB | 2 296 438 A | 7/1996 |
| WO | WO 91/00719 A1 | 1/1991 |
| WO | WO 92/11830 A2 | 7/1992 |
| WO | WO 95/05139 A1 | 2/1995 |
| WO | WO 95/13042 A1 | 5/1995 |
| WO | WO 95/17869 A1 | 7/1995 |
| WO | WO 95/17870 A1 | 7/1995 |
| WO | WO 96/00545 A1 | 1/1996 |
| WO | WO 96/03947 A1 | 2/1996 |

| | | |
|---|---|---|
| WO | WO 96/12457 A1 | 5/1996 |
| WO | WO 96/15748 A3 | 5/1996 |
| WO | WO 96/20670 A1 | 7/1996 |
| WO | WO 96/20671 A1 | 7/1996 |
| WO | WO 96/21409 A3 | 7/1996 |
| WO | WO 96/34589 A2 | 11/1996 |
| WO | WO 97/11660 A1 | 4/1997 |
| WO | WO 97/14385 A1 | 4/1997 |
| WO | WO 97/17923 A1 | 5/1997 |
| WO | WO 97/24097 A1 | 7/1997 |
| WO | WO 97/34557 A1 | 9/1997 |
| WO | WO 97/34558 A1 | 9/1997 |
| WO | WO 97/34559 A1 | 9/1997 |
| WO | WO 97/36562 A1 | 10/1997 |
| WO | WO 98/19861 A2 | 5/1998 |
| WO | WO 98/58607 A1 | 12/1998 |
| WO | WO 98/58608 A1 | 12/1998 |
| WO | WO 98/58609 A1 | 12/1998 |
| WO | WO 98/58610 A1 | 12/1998 |
| WO | WO 98/58611 A1 | 12/1998 |
| WO | WO 98/58615 A1 | 12/1998 |
| WO | WO 00/10497 A1 | 3/2000 |
| WO | WO 00/10501 A1 | 3/2000 |
| WO | WO 01/00156 A1 | 1/2001 |
| WO | WO 01/08620 A2 | 2/2001 |
| WO | WO 01/13966 A1 | 3/2001 |

OTHER PUBLICATIONS

American Society for Testing Materials (ASTM) Designation: D3236–88, "Standard Test Method for Apparent Viscosity of Hot Melt Adhesives and Coating Materials," pp. 326–331, published Dec. 1988.

Federal Test Method Standard (FTMS) No. 191A, Method 5450, "Permeability To Air; Cloth; Calibrated Orifice Method," Jul. 20, 1978, 5 pages.

Federal Test Method Standard (FTMS) No. 191A, Method 5514, "Water Resistance of Cloth; Low Range, Hydrostatic Pressure Method," Jul. 20, 1978, 3 pages.

Anderson, P.H. et al., "Faecal Enzymes: In Vivo Human Skin Irritation," *Contact Dermatitis*, vol. 30, No. 3, 1994, pp. 152–158.

Berglund, Larry G. and Frank J. Akin, "Measurement Of Air Exchange In Diapers By Tracer Gas Methods," *Tappi Journal*, vol. 80, No. 9, Sep. 1997, pp. 173–178.

Coates, Geoffrey W. and Robert M. Waymouth, "Oscillating Stereocontrol: A Strategy for the Synthesis of Thermoplastic Elastomeric Polypropylene," *Science*, vol. 267, Jan. 13, 1995, pp. 217–219.

"Molecular Weight Distributions," *Encyclopedia of Polymer Science and Engineering*, vol. 3, John Wiley & Sons, New York, 1985, pp. 299–300.

Wagener, K.B., "Oscillating Catalysts: A New Twist for Plastics," *Science*, vol. 267, Jan. 13, 1995, p. 191.

Williamson, P. and A.M. Kligman, "A New Method For Quantitative Investigation of Cutaneous Bacteria," *Journal of Investigative Dermatology*, 45:498–503, 1965.

\* cited by examiner

ABSORBENT ARTICLE WHICH MAINTAINS OR IMPROVES SKIN HEALTH

This is a division of application Ser. No. 09/379,431, Aug. 23, 1999.

BACKGROUND OF THE INVENTION

1. Field of the Invention

The present invention relates to an absorbent article for absorbing body fluids and exudates, such as urine. More particularly, the present invention relates to absorbent garments, such as disposable diapers and adult incontinence garments, which are configured to absorb body exudates while maintaining or improving the health of the wearer's skin.

2. Description of the Related Art

Many known absorbent article configurations employ absorbent materials located between a liquid pervious topsheet and a liquid impermeable backsheet. Such backsheets are well suited to prevent the migration of liquid waste from the absorbent materials to the outer garments of a wearer. Unfortunately, the use of such articles and, in particular, such articles which include a liquid and vapor impermeable backsheet can result in a high degree of humidity within the diaper when in use which may increase the temperature of the wearer's skin and result in relatively high skin hydration levels. Such conditions can lead to a reduction in the health of the wearer's skin. For example, the occlusive, moist environment inside absorbent articles incorporating such backsheets can promote the viability of microorganisms, including *Candida albicans*, which can undesirably lead to the onset of dermatitis such as what is commonly referred to as diaper rash.

Moreover, the liquid pervious topsheets on such articles have typically been constructed of nonwoven materials such as spunbond polyolefin materials. Unfortunately, such materials do not always provide a soft, nonabrasive contact with the skin. In particular, during continuous use of absorbent articles containing such topsheets, the wearer's skin can become quite irritated and red particularly in the presence of urine and feces. The abrasion resulting from such topsheets and the presence of urine and feces can also undesirably lead to the onset of dermatitis.

Diaper dermatitis can afflict almost every infant at some time during the diaper wearing years. The most severe form of this condition is usually caused by secondary infection with the fungi *Candida albicans*. Although other factors influence the pathogenesis of this fungi, one critical factor is the relative humidity within the diaper which is directly related to the occlusion or semi-occlusion of the diaper area.

In order to reduce the humidity level within diapers, breathable polymer films have been employed as outer covers for absorbent garments, such as disposable diapers. The breathable films are typically constructed with micropores to provide desired levels of liquid impermeability and air permeability. Other disposable diaper designs have been arranged to provide breathable regions in the form of breathable panels or perforated regions in otherwise vapor-impermeable backsheets to help ventilate the garment.

Moreover, to prevent body exudates from contacting the wearers skin, the caregiver often applies skin protective products directly to the skin of the wearer before positioning the article on the wearer. Such products have included petrolatum, mineral oil, talc, corn starch, or various other commercially available rash creams or lotions. This procedure typically involves the caregiver applying the products to their hand and then transferring the products to the wearer's skin.

To eliminate the caregiver from contacting the products and to reduce skin abrasion and improve skin health, some conventional absorbent articles have included lotion formulations applied to the topsheet such that, in use, the formulations transfer to the skin or provide lubricity thereby reducing the friction between the topsheet and the skin. However, conventional lotion formulations have been unstable and tended to migrate away from the surface of the topsheet into the topsheet and absorbent core of the absorbent articles leaving less on the surface to transfer to the skin or provide the reduced abrasion. This migration problem is particularly evident at higher temperatures such as those at the skin surface in use or those in typical storage conditions in warm climates.

Conventional absorbent articles, such as those described above, have not been completely satisfactory. For example, articles which employ perforated films or breathable panels can exhibit excessive leakage of liquids from the article and can excessively soil the wearer's outer garments in the regions of the perforations or panels. In addition, when the absorbent material of the article becomes loaded with liquid, the wet absorbent can block the escape of moisture from the wearer's skin. Such absorbent garment designs have not been able to maintain a high level of breathability when wet to sufficiently reduce the hydration of the wearer's skin.

Moreover, lotions which have been incorporated on the topsheets of such articles have migrated such that a less effective amount has been applied to the wearers skin or been located between the skin and the topsheet in use. Thus, large amounts of such lotions have been required to be added to the topsheet to deliver the skin benefit. As a result, the wearer's skin has remained susceptible to rashes, abrasion and irritation. Accordingly, there remains a need for absorbent articles which maintain or improve skin health.

SUMMARY OF THE INVENTION

In response to the difficulties and problems discussed above, new disposable absorbent articles which maintain or improve the health of the wearer's skin have been discovered. Such absorbent articles may have a high air exchange rate when wet, maintain skin temperature when wet, have reduced levels of skin hydration, include a lotion formulation or treatment composition which provides a skin health benefit, and/or have a reduced viability of microorganisms.

When employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

As used herein, reference to "air exchange" refers to the transfer of air and, in particular, humid air from the interior of an absorbent article, when in use on a wearer, to the exterior of the absorbent article (ambient atmosphere) which allows drier ambient air to move into the absorbent article.

As used herein, a substantially liquid impermeable material is constructed to provide a hydrohead of at least about 60 cm (centimeters), desirably at least about 80 cm, and more desirably at least about 100 cm. A suitable technique for determining the hydrohead value is the Hydrostatic Pressure Test which is described in further detail herein below.

As used herein, a substantially vapor permeable material is constructed to provide a water vapor transmission rate (WVTR) of at least about 100 g/sq.m/24 hr, desirably at least about 250 g/sq.m/24 hr, and more desirably at least about 500 g/sq.m/24 hr. A suitable technique for determining the WVTR value is the Water Vapor Transmission Rate Test which is described in further detail herein below.

As used herein, the term "viscosity" refers to the viscosity in centipoise determined according to ASTM D3236, entitled. "Standard Test Method for Apparent Viscosity of Hot Melt Adhesives and Coating Materials."

As used herein, the phrase "melting point" refers to the temperature at which the majority of the melting occurs, it being recognized that melting actually occurs over a range of temperatures.

As used herein, the phrase "melt point viscosity" refers to the viscosity of the formulation at the temperature at which the majority of the melting occurs, it being recognized that melting actually occurs over a range of temperatures.

As used herein, the phrase "penetration hardness" refers to the needle penetration in millimeters according to ASTM D 1321, "Needle Penetration of Petroleum Waxes." Lower needle penetration hardness values correspond to harder materials.

As used herein, the term "z-direction migration loss" refers to the value obtained when subjecting an absorbent article having a lotion formulation on the bodyfacing surface thereof to the Z-Direction Lotion Migration Test set forth below.

As used herein, the term "cd-direction migration loss" refers to the value obtained when subjecting an absorbent article having a lotion formulation on the bodyfacing surface thereof to the CD-Direction Lotion Migration Test set forth below.

In one aspect, the present invention relates to an absorbent article which comprises an absorbent, a front waist section, a rear waist section and an intermediate section which interconnects the front and rear waist sections. The absorbent article defines a Wet Air Exchange Rate of at least about 190 cubic centimeters per minute calculated according to the Tracer Gas Test set forth herein. In a particular embodiment, the article defines a Wet Air Exchange Rate of at least about 200, desirably at least about 225 and more desirably at least about 250 cubic centimeters per minute calculated according to the Tracer Gas Test. The absorbent article may further define a Dry Air Exchange Rate of at least about 525 cubic centimeters per minute calculated according to the Tracer Gas Test and/or a Skin Hydration Value of less than about 18 grams per square meter per hour calculated according to a Skin Hydration Test set forth herein.

In another aspect, the present invention relates to a disposable absorbent article which comprises an absorbent, a front waist section, a rear waist section and an intermediate section which interconnects the front and rear waist sections. The absorbent article defines a Skin Hydration Value of less than about 18 grams per square meter per hour calculated according to the Skin Hydration Test set forth herein. In a particular embodiment, the absorbent article may define a Skin Hydration Value of less than about 15, desirably less than about 12 and more desirably less than about 10 grams per square meter per hour calculated according to the Skin Hydration Test. The absorbent article may further define a Wet Air Exchange Rate of at least about 190 cubic centimeters per minute and/or a Dry Air Exchange Rate of at least about 525 cubic centimeters per minute calculated according to the Tracer Gas Test as set forth herein.

In another aspect, the present invention relates to a disposable absorbent article which defines a front waist section, a rear waist section, and an intermediate section which interconnects the front and rear waist sections. The absorbent article includes a) a vapor permeable backsheet which defines a Water Vapor Transmission Rate of at least about 1000 grams per square meter per 24 hours calculated according to a Water Vapor Transmission Test as set forth herein; b) a liquid permeable topsheet which is positioned in facing relation with the backsheet; and c) an absorbent body located between the backsheet and the topsheet which may define multiple zones of high air permeability for improved air exchange. In a particular embodiment, the zones of high air permeability in the absorbent body define a Frazier Porosity which is at least about 10 percent greater than a Frazier Porosity of portions of the absorbent body adjacent to the zones of high air permeability. The absorbent article may further include a ventilation layer located between the backsheet and the absorbent body.

In still another aspect, the present invention relates to a disposable absorbent article which defines a front waist section, a rear waist section, and an intermediate section which interconnects the front and rear waist sections. The absorbent article includes a) a vapor permeable, liquid impermeable backsheet which defines a Water Vapor Transmission Rate of at least about 1000 grams per square meter per 24 hours calculated according to a Water Vapor Transmission Test as set forth herein; b) a liquid permeable topsheet which is positioned in facing relation with the backsheet; c) an absorbent body located between the backsheet and the topsheet; d) a ventilation layer located between the backsheet and the absorbent body; and e) a surge management layer located between the topsheet and the absorbent body. In a particular embodiment, the absorbent body of the absorbent article includes a plurality of zones of high air permeability for improved air exchange which define a Frazier Porosity which is at least about 10 percent greater than a Frazier Porosity of portions of the absorbent body adjacent to the zones.

In yet another aspect, the present invention relates to a disposable absorbent article which includes an absorbent, a front waist section, a rear waist section and an intermediate section which interconnects the front and rear waist sections. The absorbent article defines a *C. albicans* viability which is less than about 85 percent of the *C. albicans* viability of a control calculated according to a *C. albicans* Viability Test as set forth herein. In a particular embodiment, the *C. albicans* viability is less than about 80 percent and desirably less than about 60 percent of the *C. albicans* viability of the control calculated according to the *C. albicans* Viability Test. The absorbent article may further define a Wet Air Exchange Rate of at least about 190 cubic centimeters per minute and/or a Dry Air Exchange Rate of at least about 525 cubic centimeters per minute calculated according to the Tracer Gas Test as set forth herein and/or a Skin Hydration Value of less than about 18 grams per square meter per hour calculated according to the Skin Hydration Test set forth herein.

In another aspect, the present invention relates to a disposable absorbent article which comprises an absorbent, a front waist section, a rear waist section and an intermediate section which interconnects the front and rear waist sections. The absorbent article defines a Wet Skin Temperature/Dry Skin Temperature Ratio of no more than about 1.010 calculated according to a Skin Temperature Test as set forth herein. In particular embodiments, the absorbent article defines a Wet Skin Temperature/Dry Skin Temperature Ratio of no more than about 1.005, desirably no more than about 1.000, more desirably no more than about 0.995, and even more desirably no more than about 0.990 calculated according to the Skin Temperature Test. The absorbent article may further define a Wet Air Exchange Rate of at least about 190 cubic centimeters per minute and/or a Dry Air Exchange Rate of at least about 525 cubic centimeters per minute calculated according to the Tracer Gas Test as set forth herein and/or a Skin Hydration Value of less than about 18 grams per square meter per hour calculated according to the Skin Hydration Test set forth herein.

In still another aspect, the present invention resides in an absorbent article having a topsheet which includes a lotion formulation or treatment composition on the outer bodyfacing surface thereof. In a particular embodiment, the topsheet includes a lotion formulation comprising from about 5 to about 95 weight percent of an emollient, from about 5 to about 95 weight percent of a wax, and, optionally, from about 0.1 to about 25 weight percent of a viscosity enhancer. The lotion formulation may be applied by known methods in the art such as spraying, slot coating or printing to the topsheet at a temperature no more than about 10° C. above a melting point of the lotion formulation to reduce migration of the lotion formulation on the topsheet.

In some embodiments, the emollient is selected from the group consisting of oils, esters, glycerol esters, ethers, alkoxylated carboxylic acids, alkoxylated alcohols, fatty alcohols and mixtures thereof. Moreover, in some embodiments, the wax is selected from the group consisting of animal based waxes, vegetable based waxes, mineral based waxes, silicone based waxes and mixtures thereof all of which may be natural or synthetic.

In a particular aspect, the lotion formulation includes from about 5 to about 95 weight percent of petrolatum, from about 5 to about 95 weight percent of a wax selected from the group consisting of animal based waxes, vegetable based waxes, mineral based waxes, silicone based waxes and mixtures thereof all of which may be natural or synthetic and from about 0.1 to about 25 weight percent of a polyolefin resin, all based on the total weight of the lotion formulation.

In still another aspect, the present invention resides in an absorbent article having a topsheet which includes a treatment composition on the outer bodyfacing surface thereof. The treatment composition includes a surfactant and a skin health benefit agent, preferably as an emulsion such as an oil-in-water emulsion. The skin health benefit agent may include zinc compositions. The treatment composition may also include a protein such as silk proteins like sericin.

The various aspects of the present invention advantageously provide an absorbent article with maintain or improve the health of the wearer's skin. For example, such improved absorbent articles may exhibit substantially reduced levels of hydration of the wearer's skin when in use compared to conventional absorbent articles. The reduced level of skin hydration promotes drier, more comfortable skin and renders the skin less susceptible to the viability of microorganisms. Thus, wearer's of absorbent articles made according to the present invention have reduced skin hydration and more constant skin temperatures in use which can lead to a reduction in the incidence of skin irritation and rash.

Moreover, in particular embodiments, the lotionized or treated topsheet provides a soft, smooth contact with the wearer's skin and reduced levels of skin irritation. Moreover, because the lotion formulations applied to the topsheet are more stable and have a higher viscosity than conventional lotion formulations, particularly at higher temperatures, a greater percentage of the added lotion remains on the surface of the topsheet where it can readily contact and transfer to the wearer's skin to provide the benefit. Further, if desired, a lower amount of the lotion formulation can be added to the topsheet to provide the same benefit at a lower cost due to the localization of the lotion at the surface of the topsheet. As a result, the skin of the wearers of the absorbent articles of the present invention may be less susceptible to rashes, abrasion and irritation.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

Figure 1:
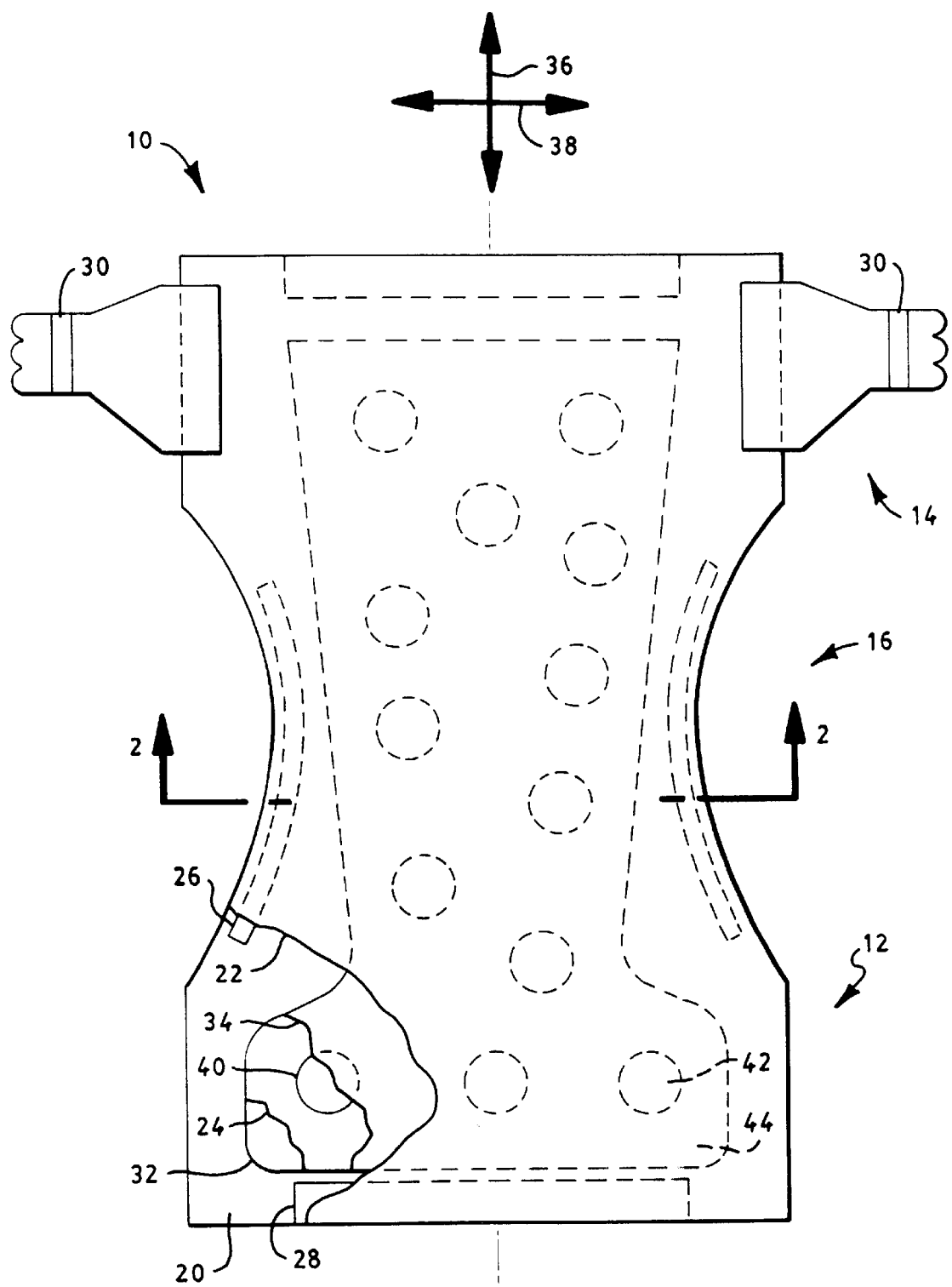
FIG. 1 representatively shows a partially cutaway, top plan view of an absorbent article according to one embodiment of the invention.

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like.

The absorbent articles of the present invention advantageously maintain or improve the health of the wearer's skin. For example, the absorbent articles may exhibit a substantially reduced level of hydration of the wearer's skin in use when compared to conventional absorbent articles. The absorbent articles of the present invention may further maintain a more constant temperature of the wearer's skin when wet when compared to conventional absorbent articles. Thus, wearer's of absorbent articles of the different aspects of the present invention have reduced skin hydration which renders the skin less susceptible to the viability of microorganisms which can lead to a reduction in the incidence of skin irritation and rash. The absorbent articles of the present invention may also deliver a lotion or other skin health benefit agent to the wearer's skin to provide improved skin health in use when compared to conventional absorbent articles.

It has been discovered that the ability of the absorbent articles of the present invention to exhibit a low level of hydration on the wearer's skin during use depends, at least in part, on the ability of the absorbent article to achieve a high rate of air exchange within the article. Moreover, it has been further discovered that the achievement of such low levels of skin hydration also depends on the ability of the article to maintain the high rate of air exchange and a more constant skin temperature even when wet.

The ability of an absorbent article to achieve high rates of air exchange both when dry and when wet has, for the purposes of this application, been quantified as the Dry Air Exchange Rate, the Wet Air Exchange Rate and the Wet Air Exchange Rate/Dry Air Exchange Rate ratio as determined according to the Tracer Gas Test set forth below. Briefly, the Tracer Gas Test involves injecting a tracer gas at a constant rate inside the absorbent article next to the skin of the wearer while the article is being worn. Simultaneously, the concentration of the tracer gas in the air space between the article and the wearer is measured by withdrawing a sample at the same constant rate as the injection. The air exchange is then determined based on mass balances of the tracer gas and the air within the space in question.

To achieve the desired low levels of skin hydration, the absorbent articles of the different aspects of the present invention may be constructed to define a Wet Air Exchange Rate of at least about 190 cubic centimeters per minute, generally at least about 200 cubic centimeters per minute, desirably at least about 225 cubic centimeters per minute, more desirably at least about 250 cubic centimeters per minute, and even more desirably at least about 300 cubic centimeters per minute. For example, the absorbent articles may define a Wet Air Exchange. Rate of from about 175 to about 1500 cubic centimeters per minute and desirably from about 225 to about 1500 cubic centimeters per minute. Absorbent articles which exhibit Wet Air Exchange Rates less than those above do not allow a sufficient amount of air exchange and undesirably result in increased levels of skin hydration. Such increased levels of skin hydration can render the skin more susceptible to the viability of microorganisms which can undesirably lead to an increase in the incidence of skin irritation and rash.

The absorbent articles of the different aspects of the present invention may further be constructed to define a Dry Air Exchange Rate of at least about 525 cubic centimeters per minute, generally at least about 575 cubic centimeters per minute, desirably at least about 625 cubic centimeters per minute, more desirably at least about 675 cubic centimeters per minute, and even more desirably at least about 750 cubic centimeters per minute for improved performance. For example, the absorbent articles may define a Dry Air Exchange Rate of from about 525 to about 2500 cubic centimeters per minute and desirably from about 575 to about 2500 cubic centimeters per minute. Absorbent articles which exhibit Dry Air Exchange Rates less than those above do not allow a sufficient amount of air exchange and undesirably result in increased levels of skin hydration. Such increased levels of skin hydration can render the skin more susceptible to the growth of microorganisms which can undesirably lead to an increase in the incidence of skin irritation and rash.

The absorbent articles of the different aspects of the present invention may further be constructed to define a Wet Air Exchange Rate/Dry Air Exchange Rate ratio of at least about 0.20, generally at least about 0.23, desirably at least about 0.27, and more desirably at least about 0.30 for improved performance. For example, the absorbent articles may define a Wet Air Exchange Rate/Dry Air Exchange Rate ratio of from about 0.20 to about 1 and desirably from about 0.23 to about 1 for improved performance.

The ability of an absorbent article to maintain a more constant skin temperature when wet has, for the purposes of this application, been quantified as the Wet Skin Temperature/Dry Skin Temperature ratio as determined according to the Skin Temperature Test set forth below. Briefly, the Skin Temperature Test involves placing the article to be tested about the forearms of test participants and measuring the temperature of the skin underneath the article before and after the article is wetted with a known amount of saline solution. The Dry Skin Temperature is recorded after the dry article has been worn for five (5) minutes. The article is then wetted and the Wet Skin Temperature is recorded after the wetted article has been worn for one hundred twenty (120) minutes.

The absorbent articles of the different aspects of the present invention may be constructed to define Wet Skin Temperature/Dry Skin Temperature ratio of no more than about 1.010, generally no more than about 1.005, desirably no more than about 1.000, more desirably no more than about 0.995, and even more desirably no more than about 0.990 for improved performance. For example, the absorbent articles may define a Wet Skin Temperature/Dry Skin Temperature ratio of from about 0.950 to about 1.010 and desirably from about 0.970 to about 1.005 for improved performance. Absorbent articles which exhibit Wet Skin Temperature/Dry Skin Temperature ratios greater than those above do not maintain skin temperature when wet which can render the skin more susceptible to the viability of microorganisms which can undesirably lead to an increase in the incidence of skin irritation and rash.

The ability of the absorbent articles of the present invention to exhibit more constant skin temperature and high levels of air exchange rate both when dry and when wet has led to reduced levels of skin hydration. The ability of an absorbent article to achieve a low level of skin hydration has, for the purposes of this application, been quantified as the Skin Hydration Value. As used herein, the term "Skin Hydration Value" refers to the value determined according to the Skin Hydration Test set forth below. In general, the Skin Hydration Value is determined by measuring the evaporative water loss on the skin of test subjects after wearing the wetted absorbent article for a set period of time.

In particular embodiments, the absorbent articles of the different aspects of the present invention may be constructed to define a Skin Hydration Value of less than about 18 grams per square meter per hour, generally less than about 15 grams per square meter per hour, desirably less than about 12 grams per square meter per hour, more desirably less than about 10 grams per square meter per hour, even more desirably less than about 8 grams per square meter per hour, and yet even more desirably less than about 5 grams per square meter per hour for improved performance. For example, the absorbent articles of the present invention may define a Skin Hydration Value of from about 0.1 to about 18 grams per square meter per hour and desirably from about 0.1 to about 12 grams per square meter per hour. Absorbent articles which exhibit Skin Hydration Values greater than those above can render the skin more susceptible to the growth of microorganisms which can undesirably lead to an increase in the incidence of skin irritation and rash.

The absorbent articles of the present invention may further exhibit reduced viability rates of microorganisms which can lead to a reduction in skin irritation. It is hypothesized that the reduced viability of microorganisms is a direct result of the increased breathability and air exchange within the articles of the present invention. The ability of an absorbent article to achieve a low rate of viability of microorganisms has, for the purposes of this application, been quantified as the *C. albicans* viability value since it is hypothesized that the presence of *Candida albicans* is directly related to the incidence of irritation and, in particular, rash. As used herein, the term "*C. albicans* viability" refers to the value determined according to the *Candida albicans* Viability Test set forth below. The *Candida albicans* Viability Test, in general, is a comparison of the *C. albicans* viability under a patch of the test absorbent article to the *C. albicans* viability under a control patch from a conventional absorbent article having a nonbreathable outer cover, i.e. an outer cover having a WVTR of less than 100 grams per square meter per 24 hours.

In particular embodiments, the absorbent articles of the different aspects of the present invention may be constructed to define a *C. albicans* viability of less than about 85 percent, generally less than about 80 percent, desirably less than about 60 percent, more desirably less than about 40 percent, and even more desirably less than about 20 percent of the *C. albicans* viability of the control for improved performance. For example, the absorbent articles of the present invention may define a *C. albicans* viability of less than about 2.5, desirably less than about 2.0, and more desirably less than about 1.75 log of *C. albicans* colony forming units when inoculated with a suspension of about 5–7 log of *C. albicans* colony forming units according to the *Candida albicans* Viability Test. Absorbent articles which exhibit *C. albicans* viability values greater than those above can undesirably lead to an increase in the incidence of skin irritation and rash. Desirably, the above *C. albicans* viability values are obtained without the incorporation of antimicrobial agents into the absorbent articles which can be perceived by consumers in a negative manner.

It has been discovered that the maintenance or improvement in the health of the wearer's skin can be achieved by selecting absorbent article constructions having a combination of one or more of the above-described properties. For example, a given level of acceptable, improved performance may be achieved by employing an absorbent article which exhibits a Dry Air Exchange Rate of at least about 525 cubic centimeters per minute and a Wet Air Exchange Rate of at least about 175 cubic centimeters per minute, and desirably a Dry Air Exchange Rate of at least about 675 cubic centimeters per minute and a Wet Air Exchange Rate of at least about 200 cubic centimeters per minute. Alternatively, improved performance can be achieved by employing an absorbent article which exhibits a Wet Air Exchange Rate of at least about 175 cubic centimeters per minute and a Skin Hydration Value of less than about 18 grams per square meter per hour, and desirably a Wet Air Exchange Rate of at least about 200 cubic centimeters per minute and a Skin Hydration Value of less than about 12 grams per square meter per hour.

Still further, it has been discovered that improved performance can be achieved by employing absorbent articles having a Dry Air Exchange Rate of at least about 525 cubic centimeters per minute and a Wet Air Exchange Rate/Dry Air Exchange Rate ratio of at least about 0.20 and desirably a Dry Air Exchange Rate of at least about 625 cubic centimeters per minute and a Wet Air Exchange Rate/Dry Air Exchange Rate ratio of at least about 0.23.

Figure 2:
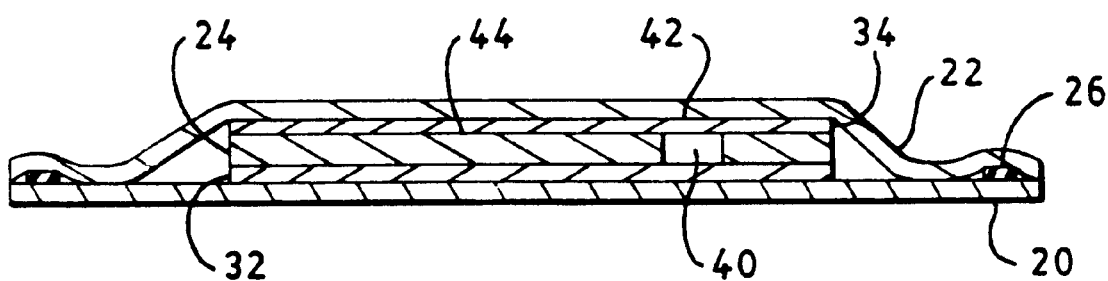
FIG. 2 representatively shows a sectional view of the absorbent article of FIG. 1 taken along line 2—2.

Examples of suitable constructions of absorbent articles for use in the present invention are described below and representatively illustrated in FIGS. 1–6. FIG. 1 is a representative plan view of an integral absorbent garment article, such as disposable diaper 10, of the present invention in its flat-out, uncontracted state (i.e., with all elastic induced gathering and contraction removed). Portions of the structure are partially cut away to more clearly show the interior construction of diaper 10, and the surface of the diaper which contacts the wearer is facing the viewer. FIG. 2 representatively shows a sectional view of the absorbent article of FIG. 1 taken along line 2—2. With reference to FIGS. 1 and 2, the disposable diaper 10 generally defines a front waist section 12, a rear waist section 14, and an intermediate section 16 which interconnects the front and rear waist sections. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs.

The absorbent article includes a vapor permeable backsheet 20, a liquid permeable topsheet 22 positioned in facing relation with the backsheet 20, and an absorbent body 24, such as an absorbent pad, which is located between the backsheet 20 and the topsheet 22. The backsheet 20 defines a length and a width which, in the illustrated embodiment, coincide with the length and width of the diaper 10. The absorbent body 24 generally defines a length and width which are less than the length and width of the backsheet 20, respectively. Thus, marginal portions of the diaper 10, such as marginal sections of the backsheet 20, may extend past the terminal edges of the absorbent body 24. In the illustrated embodiments, for example, the backsheet 20 extends outwardly beyond the terminal marginal edges of the absorbent body 24 to form side margins and end margins of the diaper 10. The topsheet 22 is generally coextensive with the backsheet 20 but may optionally cover an area which is larger or smaller than the area of the backsheet 20, as desired. The backsheet 20 and topsheet 22 are intended to face the garment and body of the wearer, respectively, while in use.

The permeability of the backsheet is configured to enhance the breathability of the absorbent article to reduce the hydration of the wearer's skin during use without allowing excessive condensation of vapor, such as urine, on the garment facing surface of the backsheet 20 which can undesirably dampen the wearer's clothes.

To provide improved fit and to help reduce leakage of body exudates from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIGS. 1 and 2, the diaper 10 may include leg elastics 26 which are constructed to operably gather and shirr the side margins of the diaper 10 to provide elasticized leg bands which can closely fit around the legs of the wearer to reduce leakage and provide improved comfort and appearance. Similarly, waist elastics 28 can be employed to elasticize the end margins of the diaper 10 to provide elasticized waists. The waist elastics are configured to operably gather and shirr the waist sections to provide a resilient, comfortably close fit around the waist of the wearer. In the illustrated embodiments, the elastic members are illustrated in their uncontracted, stretched condition for the purpose of clarity.

Fastening means, such as hook and loop fasteners 30, are employed to secure the diaper on a wearer. Alternatively, other fastening means, such as buttons, pins, snaps, adhesive tape fasteners, cohesives, mushroom-and-loop fasteners, or the like, may be employed.

The diaper 10 may further include other layers between the absorbent body 24 and the topsheet 22 or backsheet 20. For example, as representatively illustrated in FIGS. 1 and 2, the diaper 10 may include a ventilation layer 32 located between the absorbent body 24 and the backsheet 20 to insulate the backsheet 20 from the absorbent body 24 to improve air circulation and effectively reduce the dampness of the garment facing surface of the backsheet 20. The ventilation layer 32 may also assist in distributing fluid exudates to portions of the absorbent body 24 which do not directly receive the insult. The diaper 10 may also include a surge management layer 34 located between the topsheet 22 and the absorbent body 24 to prevent pooling of the fluid exudates and further improve air exchange and distribution of the fluid exudates within the diaper 10.

The diaper 10 may be of various suitable shapes. For example, the diaper may have an overall rectangular shape, T-shape or an approximately hour-glass shape. In the shown embodiment, the diaper 10 has a generally I-shape. The diaper 10 further defines a longitudinal direction 36 and a lateral direction 38. Other suitable diaper components which may be incorporated on absorbent articles of the present invention include containment flaps, waist flaps, elastomeric side panels, and the like which are generally known to those skilled in the art.

Examples of diaper configurations suitable for use in connection with the instant application which may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 10 are integrally assembled together employing various types of suitable attachment means, such as adhesive, sonic bonds, thermal bonds or combinations thereof. In the shown embodiment, for example, the topsheet 22 and backsheet 20 are assembled to each other and to the absorbent body 24 with lines of adhesive, such as a hot melt, pressure-sensitive adhesive. Similarly, other diaper components, such as the elastic members 26 and 28, fastening members 30, and ventilation and surge layers 32 and 34 may be assembled into the diaper article by employing the above-identified attachment mechanisms.

The backsheet 20 of the diaper 10, as representatively illustrated in FIGS. 1 and 2, is composed of a substantially vapor permeable material. The backsheet 20 is generally constructed to be permeable to at least water vapor and has a water vapor transmission rate of at least about 1000 g/sq.m/24 hr., desirably at least about 1500 g/sq.m/24 hr, more desirably at least about 2000 g/sq.m/24 hr., and even more desirably at least about 3000 g/sq.m/24. For example, the backsheet 20 may define a water vapor transmission rate of from about 1000 to about 6000 g/sq.m/24 hr. Materials which have a water vapor transmission rate less than those above do not allow a sufficient amount of air exchange and undesirably result in increased levels of skin hydration.

The backsheet 20 is also desirably substantially liquid impermeable. For example, the backsheet may be constructed to provide a hydrohead value of at least about 60 cm, desirably at least about 80 cm, and more desirably at least about 100 cm when subjected to the Hydrostatic Pressure Test. Materials which have hydrohead values less than those above undesirably result in the strike through of liquids, such as urine, during use. Such fluid strike through. can undesirably result in a damp, clammy feeling on the backsheet 20 during use.

The backsheet 20 may be composed of any suitable materials which either directly provide the above desired levels of liquid impermeability and air permeability or, in the alternative, materials which can be modified or treated in some manner to provide such levels. In one embodiment, the backsheet 20 may be a nonwoven fibrous web constructed to provide the required level of liquid impermeability. For example, a nonwoven web composed of spunbonded or meltblown polymer fibers may be selectively treated with a water repellent coating or laminated with a liquid impermeable, vapor permeable polymer film to provide the backsheet 20. In a particular embodiment of the invention, the backsheet 20 may comprise a nonwoven web composed of a plurality of randomly deposited hydrophobic thermoplastic meltblown fibers which are sufficiently bonded or otherwise connected to one another to provide a substantially vapor permeable and substantially liquid impermeable web. The backsheet 20 may also comprise a vapor permeable nonwoven layer which has been partially coated or otherwise configured to provide liquid impermeability in selected areas.

Examples of suitable materials for the backsheet 20 are also described in U.S. Pat. No. 5,482,765 issued Jan. 9, 1996 in the name of Bradley et al. and entitled "NONWOVEN FABRIC LAMINATE WITH ENHANCED BARRIER PROPERTIES"; U.S. patent application Ser. No. 08/622,903 filed Mar. 29, 1996 in the name of Odorzynski et al. and entitled "ABSORBENT ARTICLE HAVING A BREATHABILITY GRADIENT"; U.S. patent application Ser. No. 08/668,418 filed Jun. 21, 1996, in the name of Good et al. and entitled "ABSORBENT ARTICLE HAVING A COMPOSITE BREATHABLE BACKSHEET"; and U.S. patent application Ser. No. 08/882,712 filed Jun. 25, 1997, in the name of McCormack et al. and entitled "LOW GAUGE FILMS AND FILM/NONWOVEN LAMINATES", the disclosures of which are herein incorporated by reference.

In a particular embodiment, the backsheet 20 is provided by a microporous film/nonwoven laminate material comprising a spunbond nonwoven material laminated to a microporous film. The spunbond nonwoven comprises filaments of about 1.8 denier extruded from a copolymer of ethylene with about 3.5 weight percent propylene and defines a basis weight of from about 17 to about 25 grams per square meter. The film comprises a cast coextruded film having calcium carbonate particles therein and defines a basis weight of about 58 grams per square meter prior to stretching. The film is preheated, stretched and annealed to form the micropores and then laminated to the spunbond nonwoven. The resulting microporous film/nonwoven laminate based material has a basis weight of from about 30 to about 60 grams per square meter and a water vapor transmission rate of from about 3000 to about 6000 g/sq.m/24 hr. Examples of such film/nonwoven laminate materials are described in more detail in U.S. patent application Ser. No. 08/882,712 filed Jun. 25, 1997, in the name of McCormack et al. and entitled "LOW GAUGE FILMS AND FILM/ NONWOVEN LAMINATES", the disclosure of which has been incorporated by reference.

The topsheet 22, as representatively illustrated in FIGS. 1 and 2, suitably presents a bodyfacing surface which is compliant, soft feeling, and nonirritating to the wearer's skin. Further, the topsheet 22 may be less hydrophilic than the absorbent body 24, to present a relatively dry surface to the wearer, and may be sufficiently porous to be liquid permeable, permitting liquid to readily penetrate through its thickness. A suitable topsheet 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 22 is suitably employed to help isolate the wearer's skin from liquids held in the absorbent body 24.

Various woven and nonwoven fabrics can be used for the topsheet 22. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 22 comprises a nonwoven, spunbond, polypropylene fabric composed of about 2.8–3.2 denier fibers formed into a web having a basis weight of about 22 grams per square meter and a density of about 0.06 gram per cubic centimeter.

In a particular embodiment of the present invention, the topsheet 22 may be surface treated with about 0.3 weight percent of a surfactant mixture which contains a mixture of AHCOVEL Base N-62 and GLUCOPON 220UP surfactant in about a 3:1 ratio based on a total weight of the surfactant mixture. The AHCOVEL Base N-62 is purchased from Hodgson Textile Chemicals Inc., a business having offices in Mount Holly, N.C., and includes a blend of hydrogenated ethoxylated castor oil and sorbitan monooleate in a 55.45 weight ratio. The GLUCOPON 220UP is purchased from Henkel Corporation and includes alkyl polyglycoside. The surfactant may also include additional ingredients such as aloe. The surfactant may be applied. by any conventional means, such as spraying, printing, brush coating, foam or the like. The surfactant may be applied to the entire topsheet 22 or may be selectively applied to particular sections of the topsheet 22, such as the medial section along the longitudinal centerline of the diaper, to provide greater wettability of such sections.

The topsheet 22 of the absorbent article of the present invention may further include a lotion formulation on the outer bodyfacing surface thereof. The lotion formulation may generally include an emollient, a wax and, optionally, a viscosity enhancer. For example, the lotion formulation may include from about 5 to about 95 weight percent of an emollient, from about 5 to about 95 weight percent of a wax, and from about 1 to about 25 weight percent of a viscosity enhancer based on a total weight of the lotion formulation. The lotion formulation may include other ingredients as well.

The emollients act as lubricants to reduce the abrasiveness of the topsheet to the skin and, upon transfer to the skin, help to maintain the soft, smooth and pliable appearance of the skin. Suitable emollients which can be incorporated into the lotion formulation include oils such as petroleum based oils, vegetable based oils, mineral oils, natural or synthetic oils, silicone oils, lanolin and lanolin derivatives, kaolin and kaolin derivatives and the like and mixtures thereof; esters such as cetyl palmitate, stearyl palmitate, cetyl stearate, isopropyl laurate, isopropyl myristate, isopropyl palmitate and the like and mixtures thereof; glycerol esters; ethers such as eucalyptol, cetearyl glucoside, dimethyl isosorbicide polyglyceryl-3 cetyl ether, polyglyceryl-3 decyltetradecanol, propylene glycol myristyl ether and the like and mixtures thereof; alkoxylated carboxylic acids; alkoxylated alcohols; fatty alcohols such as octyldodecanol, lauryl, myristyl, cetyl, stearyl and behenyl alcohol and the like and mixtures thereof; and the like and mixtures thereof. For example, a particularly well suited emollient is petrolatum. Other conventional emouients may also be added in a manner which maintains the desired properties of the lotion formulations set forth herein.

To provide the improved stability and transfer to the skin of the wearer, the lotion formulation may include from about 5 to about 95 weight percent, desirably from about 20 to about 75 weight percent, and more desirably from about 40 to about 60 weight percent of the emollient. Lotion formulations which include an amount of emollient greater than the recited amounts tend to have lower viscosities which Undesirable leads to migration of the lotion. Whereas, lotion formulations which include an amount of emollient less than the recited amounts tend to provide less transfer to the wearer's skin;

The wax in the lotion formulations of the present invention primarily functions as an immobilizing agent for the emollient and any active ingredient. In addition to immobilizing the emollient and reducing it's tendency to migrate, the wax in the lotion formulation provides a tackiness to the lotion formulation which improves the transfer to the skin of the wearer. The presence of the wax also modifies the mode of transfer in that the lotion tends to fracture or flake off instead of actually rubbing off onto the skin of the wearer which can lead to improved transfer to the skin. The wax may further function as an emollient, occlusive agent, moisturizer, barrier enhancer and combinations thereof.

Suitable waxes which can be incorporated into the lotion formulation include animal, vegetable, mineral or silicone based waxes which may be natural or synthetic such as, for example, bayberry wax, beeswax, C30 alkyl dimethicone, candelilla wax, carnauba, ceresin, cetyl esters, esparto, hydrogenated cottonseed oil, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcryustalline wax, mink wax, motan acid wax, motan wax, ouricury wax, ozokerite, paraffin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, synthetic jojoba wax, synthetic wax, and the like and mixtures thereof. For example, a particularly well suited wax includes about 70 weight percent ceresin wax, about 10 weight percent microcrystalline wax, about 10 weight percent paraffin wax and about 10 weight percent cetyl esters (synthetic spermaceti wax).

To provide the improved transfer to the skin of the wearer, the lotion formulation may include from about 5 to about 95 weight percent, desirably from about 25 to about 75 weight percent, and more desirably from about 40 to about 60 weight percent of the wax. Lotion formulations which include an amount of wax less than the recited amounts tend to have lower viscosities which undesirable leads to migration of the lotion. Whereas, lotion formulations which include an amount of wax greater than the recited amounts tend to provide less transfer to the wearer's skin.

A viscosity enhancer may be added to the lotion formulation to increase the viscosity to help stabilize the formulation on the bodyfacing surface of the topsheet 22 and thereby reduce migration and improve transfer to the skin. Desirably, the viscosity enhancer increases the viscosity of the lotion formulation by at least about 50 percent, more desirably at least about 100 percent, even more desirably by at least about 500 percent, yet even more desirably by at least about 1000 percent, and even more desirably by at least about 5000 percent. Suitable viscosity enhancers which can be incorporated into the lotion formulation include polyolefin resins, lipophilic/oil thickeners, ethylene/vinyl acetate copolymers, polyethylene, silica, talc, colloidal silicone dioxide, zinc stearate, cetyl hydroxy ethyl cellulose and other modified celluloses and the like and mixtures thereof. For example, a particularly well suited viscosity enhancer is an ethylene/vinyl acetate copolymer commercially available from E. I. Dupont De Ne Mours under the trade designation ELVAX.

To provide the improved transfer to the skin of the wearer, the lotion formulation may include from about 0.1 to about 25 weight percent, desirably from about 5 to about 20 weight percent, and more desirably from about 10 to about 15 weight percent of the viscosity enhancer for reduced migration and improved transfer to the wearer's skin.

If it is desired that the lotion formulation treat the skin, it can also include an active ingredient such as a diaper rash skin protectant. Skin protectants are a drug product which protects injured or exposed skin or mucous membrane surface from harmful or annoying stimuli. Suitable active ingredients, in addition to those mentioned above as suitable emollients, which can be incorporated into the lotion formulation include, but are not limited to, alantoin and its derivatives, aluminum hydroxide gel, calamine, cocoa butter, dimethicone, cod liver oil, glycerin, kaolin and its derivatives, lanolin and its derivatives, mineral oil, shark liver oil, talc, topical starch, zinc acetate, zinc carbonate, and zinc oxide and the like, and mixtures thereof. The lotion formulation may include from about 0.10 to about 95 weight percent of the active ingredient depending upon the skin protectant and the amount desired to be transferred to the skin.

In order to better enhance the benefits to the wearer, additional ingredients can be included in the lotion formulations of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product that checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal), silicones/organomodified silicones (protection, tissue water resistance, lubricity, tissue softness), oils (mineral, vegetable, and animal),; natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

An important property of the lotion formulations of the different aspects of the present invention is their ability to remain on the surface of the topsheet and their resistance to migration into the article such that they can readily be transferred to the wearer's skin. In this regard, the articles having the lotion formulations of the present invention applied to there topsheet define a z-direction migration loss of no more than about 55%, desirably no more than about 50%, more desirably no more than about 45%, even more desirably no more than about 40% and yet even more desirably no more than about 35% when subjected to the Z-Direction Lotion Migration Test set forth below. In articles which have a greater z-direction migration loss, the lotion formulation undesirably migrates into the interior and along the surface of the topsheet and at times through the topsheet into the absorbent body of the article which results in a lower reduction in abrasion and less transfer to the skin of the wearer.

Another important measure of the lotion formulations of the different aspects of the present invention is their ability to resist migration laterally along the surface of the topsheet. In this regard, the articles having the lotion formulations of the present invention applied to the topsheet define a cd-direction migration loss of no more than about 40%, adesirably no more than about 35%, more desirably no more than about 30%, even more desirably no more than about 25% and yet even more desirably no more than about 20% when subjected to the CD-Direction Lotion Migration Test set forth below. In articles which have a greater cd-direction migration loss, the lotion formulation undesirably migrates along the surface of the topsheet and at times through the topsheet into the absorbent body of the article which results in a lower reduction in abrasion and less transfer to the skin of the wearer.

Moreover, to provide the improved stability and transfer to the skin of the wearer, the lotion formulation of the present invention may define a melting point of from about 30° C. to about 1000° C., desirably from about 350° C. to about 800° C., and more desirably from about 400° C. to about 75° C. Lotion formulations which have lower melting points exhibit migration of the lotion during use and at elevated temperatures in storage which can undesirably result in reduced transfer to the skin. Whereas, lotion formulations which have higher melting points may require that the lotion be at a temperature above the flash point of the topsheet material which can undesirably lead to fires.

The lotion formulation of the present invention may further define a melt point viscosity of from about 50 to about 1000000 centipoise, desirably from about 50000 to about 800000 centipoise, and more desirably from about 100000 to about 500000 centipoise for reduced migration and improved transfer to the skin of the wearer. Lotion formulations which have lower melt point viscosities exhibit migration of the lotion through the topsheet into the absorbent body of the article which can undesirably result in reduced transfer to the skin. Whereas, lotion formulations which have higher melt point viscosities may be so solid as to also exhibit a reduced transfer to the skin.

Further, to provide the improved stability and transfer to the skin of the wearer, the lotion formulation of the present invention may also define a viscosity of from about 50 to about 10000 centipoise, desirably from about 100 to about 500 centipoise, and more desirably from about 150 to about 250 centipoise at a temperature of 60° C. Lotion formulations which have lower viscosities at 60° C. exhibit migration of the lotion through the topsheet into the absorbent body of the article which can undesirably result in reduced transfer to the skin. Whereas, lotion formulations which have higher viscosities at 60° C. may be so solid as to also exhibit a reduced transfer to the skin.

The penetration hardness of the lotion formulations of this invention can be from about 5 to about 360 millimeters, more desirably from about 10 to about 200 millimeters, more desirably from about 20 to about 150 millimeters, and still more desirably from about 40 to about 100 millimeters. (Lotion formulations having a needle penetration hardness greater than 360 millimeters cannot be measured using ASTM method D 1321). The hardness of the lotion formulations of this invention is important for two reasons. First, the softer the formulation the more mobile the formulation will be, making the formulation more likely to migrate to the inner plies of the tissue, which is not desirable. Secondly, softer formulations tend to be more greasy/oily to the touch, which is also less desirable. In general, formulations having a needle penetration hardness of from about 200 to about 360 millimeters feel creamy to slightly greasy with less smoothness (depending on additives). Formulations that have needle penetration hardness values of from about 5 to about 200 millimeters feel silky to creamy and very smooth (depending on additives).

The lotion formulation may be applied to the entire bodyfacing surface of the topsheet 22 or may be selectively applied to particular sections of the bodyfacing surface, such as the medial section along the longitudinal centerline of the diaper, to provide greater lubricity of such sections and to transfer such lotion to the wearer's skin. Alternatively, the bodyfacing surface of the topsheet 22 may include multiple stripes of the lotion formulation applied thereto. For example, the bodyfacing surface of the topsheet 22 may include from 1 to 10 stripes of lotion formulation extending along the longitudinal direction of the diaper 20. The stripes may extend the full length of the topsheet 22 or only a portion thereof. The stripes may also define a width of from about 0.2 to about 1 centimeters.

The lotion formulation should cover a sufficient amount of the surface area of the topsheet 22 to ensure adequate transfer to the skin and reduced abrasion between the topsheet 22 and the wearer's skin. Desirably, the lotion formulation is applied to at least about 5 percent and more desirably at least about 25 percent of the bodyfacing surface of the topsheet 22.

The lotion formulation can be applied to the topsheet at any add-on level which provides the desired transfer benefit. For example, the total add-on level of the lotion formulation can be from about 0.05 to about 100 mg/cm$^2$, desirably from about 1 to about 50 mg/cm$^2$ and more desirably from about 10 to about 40 mg/cm$^2$ for improved performance. The add-on amount will depend upon the desired effect of the lotion on the product attributes and the specific lotion formulation. As discussed above, the improved stability and reduced tendency to migrate of the lotion formulations of the present invention allows a lesser amount of lotion to be applied to the topsheet 22 to achieve the same benefit when compared with conventional lotion formulations.

The lotion formulation may be applied to the topsheet 22 in any of many well known manners. A preferred method to uniformly apply the lotion formulation to the surface of the topsheet 22 is spraying or slot coating, because it is the most exact process and offers maximum control of the formulation distribution and transfer rate. However, other methods, such as rotogravure or flexographic printing, can be used.

For example, the lotion formulation may be applied to the topsheet 22 by (a) heating the lotion formulation to a temperature above the melting point of the formulation, causing the formulation to melt, (b) uniformly applying the melted formulation to the bodyfacing surface of the topsheet; and (c) resolidifying the deposits of the melted formulation. Desirably, resolidification of the deposits occurs almost instantaneously, without the need for external cooling means such as chill rolls. This can occur if the formulation is heated to a temperature only slightly above or at the melting point of the formulation. However, external means such as chill rolls, either before or after the application of melt, can be used if desired to accelerate resolidification.

The increased viscosity of the lotion at the process temperature and the instantaneous resolidification tends to impede penetration of the formulation into the topsheet and absorbent body of the article and retain it on the bodyfacing surface of the topsheet 22, which is advantageous. For example, the temperature of the melted formulation can advantageously be less than about 10° C., more desirably less than about 5° C., and still more desirably less than about 2° C. above the melting point of the formulation prior to applying it to the topsheet for reduced migration. As the temperature of the melted formulation approaches the melting point of the formulation, the viscosity of the melted formulation generally increases, which further enhances the tendency of the melted formulation to be retained on the surface.

The topsheet 22 of the absorbent article of the present invention may further include a skin treatment composition on the outer bodyfacing surface thereof for preserving and restoring the natural integrity of the skin. This is achieved by depositing a skin health benefit agent from the topsheet 22 which may control the release of the agent to the surface of the skin. The skin health benefit agent may act as a protectorant that is capable of maintaining the pH of the skin, inhibiting the activity of irritants to the skin, and maintaining skin hydration and lubrication. Suitable skin treatment compositions are described in commonly assigned U.S. patent application Ser. No. 60/141788 filed Jun. 30, 1999 in the name of Tyrrell et al. (Attorney Docket No. 13,949), which is herein incorporated by reference.

Pancreatic digestive enzymes that are expelled by the body with feces have been implicated to induce skin inflammation (Anderson, P. H., Bucher, A. P., Saees, II, Lee, P. C., Davis, J. A., and Maibach, H. I., Faecal enzymes: in vivo skin irritation. *Contact Dermatitis* 1994; 30, 152–158). When the feces, including these enzymes, contact the skin, the skin becomes irritated. In some cases, these enzymes as well as others found in feces and urine, can cleave stratum corneum proteins, thereby breaking down the natural protective barrier of the skin. The skin becomes susceptible to irritation directly by these enzymes or indirectly by other "irritants" in the feces and urine that are now accessible to the viable tissue. The lotion formulations and treatment compositions of the present invention may be designed to form a thin, tenacious, substantially continuous film over the skin to inhibit, or at least minimize, the effect of such irritants.

The treatment composition of the present invention includes a surfactant and a skin health benefit agent.

Preferably, the treatment composition is prepared as an emulsion of the surfactant and skin health benefit agent, usually as an oil-in-water (o/w) emulsion.

Examples of emulsions include aqueous emulsions of a skin health benefit agent, e.g. zinc sulfate heptahydrate, and a surfactant such as AHCOVEL Base N-62. It has been found that when emulsions containing about 75 wt. % surfactant and up to about 25 wt. % skin health benefit agent at about 0.1 to 40 wt. % total solids are used, sufficient amounts of the skin health benefit agent transfer to the skin. Preferably, the emulsions will contain between about 5 to 30 wt. % solids. These emulsions can either be applied onto a substrate from a high-solids bath (up to 40 wt. %) or from dilute baths ranging from 0.1 wt. % to about 20 wt. %. Preferably, the emulsion will be diluted to about 0.5 wt. % to about 15 wt. %.

The surfactants useful in the treatment compositions of the present invention are selected to provide superior fluid handling performance, skin protection and mildness to human skin. Useful examples of suitable surfactants include ethoxylated hydrogenated fatty oils, monosaccharides, monosaccharides derivatives, polysaccharides, polysaccharide derivatives, and combinations thereof.

Water miscible nonionic surfactants are preferred and such surfactants are commercially available. Examples of such surfactants include AHCOVEL and GLUCOPON 220UP, which is an alkylpolyglycoside having 8 to 10 carbons in the alkyl chain, and may also be used as a part of the surfactant. Other well known nonionic surfactants are the primary aliphatic alcohol ethoxylates, secondary aliphatic alcohol ethoxylates, alkylphenol ethoxylates and ethyleneoxide-propylene oxide condensates on primary alkanols, such as PLURAFACS and PLURONICS (available from BASF, Inc.) and condensates of ethylene oxide with sorbitan fatty acid esters such as TWEEN (also available from Uniqema). The nonionic surfactants generally are the condensation products of an organic aliphatic or alkyl aromatic hydrophobic compound and hydrophilic ethylene oxide group. Practically any hydrophobic compound having a carboxy, hydroxy, amido, or amino group with a free hydrogen attached to the nitrogen can be condensed with ethylene oxide or with the polyhydration product thereof, polyethylene glycol, to form a water miscible nonionic surfactant. Other suitable surfactants include polyoxyethylene sorbitan monolaurate, polyoxyethylene sorbitan monostearate, polyoxyethylene sorbitan trioleate, polyoxyethylene sorbitan tristearate, and bovine lipid extract surfactant (Survanta, Ross Laboratories), a drug used to treat Acute Respiratory Distress Syndrome and Cystic Fibrosis, and enzymes such as papain or pepsin which cleave protein structures.

More specifically, the nonionic surfactant may include the condensation products of a higher alcohol (e.g., an alkanol containing about 8, 9, 10, 11, 12, 13, 14, 15, 16, 17 or 18 carbon atoms in a straight or branched chain configuration) condensed with about 5 to 30 moles of ethylene oxide. Examples include: lauryl or myristyl alcohol condensed with about 16 moles of ethylene oxide (EO); tridecanol condensed with about 6 moles of EO; myristyl alcohol condensed with about 10 moles of EO per mole of myristyl alcohol; the condensation product of EO with a cut of coconut fatty alcohol containing a mixture of fatty alcohols with alkyl chains varying from 10, 11, 12, 13 or 14 carbon atoms in length and wherein the condensate contains either about 6 moles of EO per mole of total alcohol or about 9 moles of EO per mole of alcohol; and tallow alcohol ethoxylates containing 6 EO to 11 EO per mole of alcohol. Condensates of 2 to 30 moles of ethylene oxide with sorbitan mono- and 3$C_{10}$–$C_{20}$ alkanoic acid esters having a HLB (hydrophilicilipophilic balance) of about 4 to 20, preferably about 8 to 15, may also be employed as the nonionic surfactant.

Another class of surfactant compounds include the alkyl polysaccharides. Alkyl polysaccharides are alkyl polyglycosides having the formula SUGAR-O-R, where R is a hydrophobic group.

Suitable skin health benefit agents for use in the treatment compositions of the present invention include zinc compositions to reduce or prevent skin irritation and/or acute inflammatory reactions of the skin. Examples of such agents include zinc salt, zinc sulfate monohydrate, and the like. Advantageously, the zinc salt will be present in the composition as an aqueous emulsion. These agents are useful as astringents and enzyme inhibitors, and more particularly useful in inhibiting both fecal and urine proteases. Zinc can interact with the catalytic site of the protease, in particular, the class of proteases known as serine proteases, to inhibit proteolytic activity. By inhibiting the proteolytic activity, the intent is to keep the skin from ever becoming irritated, rather than treating the skin once it has become irritated.

A further advantage of the skin health benefit agent of the present invention relates to lowering the pH. The serine proteases, e.g. trypsin and pancreatic elastase, which are present in, for example, feces and urine, are catalytically optimal at a basic pH of approximately 8.0 and 8.5, respectively. The skin health benefit agent of the present invention has unexpectedly been found to lower the pH, thereby decreasing the catalytic efficiency of these proteases.

The skin health benefit agent is present in the treatment compositions of the present invention in the range of from about 0.01% to about 10% by weight of the treatment composition. Preferably, the agent will be present in the amount of about 0.25% to about 1% by weight of the treatment composition.

The treatment compositions of the present invention may also include a protein that can be administered topically in a controlled manner. One such protein is sericin. Sericin is one of two proteins that are part of the twin fibroin silk thread spun by Bombyx Mori, a domestic insect. Sericin acts as a protective envelope around the fibroin thread as it is spun, which is like spinning of fibers with soluble sizing agents to help form good quality fibers. The sericin can be easily separated from silk protein by hydrolysis. Post-spun sericin, with its unique properties, is known to have high affinity to a number of proteins. When refined to a high molecular weight substance it is amenable to binding to the keratin of skin and hair, forming a resistant, moisturizing, and protective film on the skin/hair, imparting good barrier properties.

Sericin is a silk protein obtained by controlled hydrolysis of low molecular weight silk having a specific gravity of at least about 1. A commercially available silk protein is available from Croda, Inc., of Parsippany, N.J., and is sold under the trade name CROSILK LIQUID (silk amino acids), CROSILK 10,000 (hydrolyzed silk), CROSILK POWDER (powdered silk), and CROSILKQUAT (cocodimonium hydroxypropyl silk amino acid). Another example of a commercially available silk protein is SERICIN, available from Pentapharm, LTD, a division of Kordia, by, of the Netherlands. Further details of such silk protein mixtures can be found in U.S. Pat. No. 4,906,460, to Kim, et al., assigned to Sorenco, which is herein incorporated by reference in its entirety.

The silk protein derivatives may be chosen from one of several potential compositions. Included among the silk derivatives are silk fibers and hydrolysate of silk fibers. The silk fibers may be used in the form of powder in preparing the emulsion or as a powder of a product obtained by washing and treating the silk fibers with an acid. Preferably, silk fibers are used as a product obtained by hydrolysis with an acid, alkali or enzyme, as disclosed in U.S. Pat. No. 4,839,168 to Abe et al.; U.S. Pat. No. 5,009,813 to Watanube et al., and U.S. Pat. No. 5,069,898 to Goldberg, each incorporated herein by reference in its entirety.

Another silk derivative that may be employed in the composition of the present invention is protein obtained from degumming raw silk, as disclosed, for example, in U.S. Pat. No. 4,839,165 to Hoppe et al., incorporated herein by reference in its entirety. The principal protein obtained from the raw silk is sericin, which has an empirical formula of $C_{15}H_{25}O_3N_5$ and a molecular weight of about 323.5.

A preferred silk derivative is a mixture of two or more individual amino acids, which naturally occur in silk. The principal silk amino acids are glycine, alanine, serine and tyrosine.

Another example of a silk derivative for use in the emulsion composition of the present invention is a fine powder of silk fibroin in nonfibrous or particulate form, as disclosed in U.S. Pat. No. 4,233,212 to Otoi et al., incorporated herein by reference in its entirety. The fine powder is produced by dissolving a degummed silk material in at least one solvent selected from, for example, an aqueous cupriethylene diamine solution, an aqueous ammonia solution of cupric hydroxide, an aqueous alkaline solution of cupric hydroxide and glycerol, an aqueous lithium bromide solution, an aqueous solution of the chloride, nitrate or thiocyanate of calcium, magnesium or zinc and an aqueous sodium thiocyanate solution. The resulting fibroin solution is then dialyzed. The dialyzed aqueous silk fibroin solution, having a silk fibroin concentration of from about 3 to 20% by weight, is subjected to at least one treatment for coagulating and precipitating the silk fibroin, such as, for example, by the addition of a coagulating salt, by aeration, by coagulation at the isoelectric point, by exposure to ultrasonic waves, by agitation at high shear rate and the like. The resulting product is a silk fibroin gel, which may be incorporated directly into a treatment composition or the same may be dehydrated and dried into a powder and then dissolved in the treatment composition.

The silk material used to form the silk fibroin includes cocoons, raw silk, waste cocoons, raw silk waste, silk fabric waste and the like. The silk material is degummed or freed from sericin by a conventional procedure such as, for example, by washing in warm water containing a surfactant-active agent or an enzyme, and then dried. The degummed material is dissolved in the solvent and preheated to a temperature of from about 60 to 95° C., preferably of from about 70 to 85° C. Further details of the process of obtaining the silk fibroin are discussed in previously referenced U.S. Pat. No. 4,233,212.

In addition to the silk protein in the treatment compositions of the present invention, an additional protein may be present in the amount of about 0.1 to about 4.0% by weight. This additional protein may be selected from the group consisting of hydrolyzed animal collagen protein obtained by an enzymatic hydrolysis, lexeine protein, vegetal protein and hydrolyzed wheat protein and mixtures thereof.

The treatment compositions of the present invention can be in the form of an oil-in-water (o/w) emulsion or after dilution with water, with the essential ingredients being water, surfactant, and/or co-surfactant.

Because the composition as prepared is an aqueous liquid formulation and since no particular mixing is required to form the o/w emulsion, the composition is easily prepared simply by combining all the ingredients in a suitable vessel or container. The order of mixing the ingredients is not particularly important and generally the various ingredients can be added sequentially or all at once or in the form of aqueous emulsions of each or all of the primary surfactants and co-surfactants can be separately prepared and combined with each other. It is important to note that emulsions of, for instance, organic acid emulsions would not be acceptable for use in the present invention, since such emulsions would be a strong skin irritant and counterproductive to the intended use of the present invention. The protein, when present, can be added as an aqueous emulsion thereof or can be added directly. It is not necessary to use elevated temperatures in the formation step and room temperature is sufficient. However, higher temperatures of up to about 180° F. (82.20° C.), preferably 110 to 140° F. (43.3 to 60° C.), can also be used.

For administration to the skin of a human or other mammal, the treatment compositions will often be sterilized or formulated to contain one or more preservatives for incorporation into pharmaceutical, cosmetic or veterinary formulations. These treatment compositions can be sterilized by conventional, well-known sterilization techniques, e.g., boiling or pasteurization, without substantially adversely affecting the biological activity of the composition. The compositions may contain pharmaceutically acceptable auxiliary substances as required to approximate physiological conditions and as necessary to prepare compositions for convenient administration, such as those described above in connection with the description of the lotion formulation, such as pH adjusting and buffering agents, preservatives, and delivery vehicles. Actual methods for preparing pharmaceutically administrable compounds will be known or apparent to those skilled in the art and are described in detail in, for example, Remington's Pharmaceutical Science, supra.

Perfumes, dyes and pigments can also be incorporated into the treatment compositions of the invention. For semi-solid compositions, as would be appropriate for pastes and creams intended for topical administration, the peptone-copper complexes can be provided separately or may be compounded with conventional nontoxic carriers such as, for example, aloe vera gel, squalene, glycerol stearate, polyethylene glycol, cetyl alcohol, stearic acid, and propylene glycol, among others. Such compositions may contain about 5–100% active ingredients, more preferably about 5–25%.

The treatment compositions may be administered to a wearer of the article with un-compromised skin or in situations where a subject is already suffering from damaged skin (e.g., peeling) due to ultraviolet or other irradiation or oxidative skin damage. The treatment compositions incorporated onto the topsheet 22 such that they are administered in an amount sufficient to allow inhibition of further damage by topically administered irritating substances or other unknown irritating substances and are more effective than if the host were not treated. Amounts adequate to accomplish these effects are defined as a "therapeutically effective dose" and will vary according to the application.

In prophylactic and cosmetic applications, the treatment compositions are employed for protecting the skin from damage. Thus, the skin health benefit agents and/or silk proteins are administered to a host under conditions which protect the integrity of the skin, maintains physiological pH, skin hydration and lubrication. In these uses, the precise amounts again depend on the amount of protection desired and the extent and conditions under which the skin is exposed to potentially damaging conditions, such as those caused by fecal and urine proteases, or other irritating substances. They can generally range from about 0.1 mg to about 10 mg per day per square centimeter of skin. Single or multiple administrations of the compositions can be carried out daily or over a prolonged period of time.

The silk proteins of the invention may be administered to the skin in relatively large amounts without serious side effects, although indiscriminate use may produce irritation of the skin. In instances where the compositions are administered prophylactically to inhibit oxidative or biochemical damage to the skin or to those suffering from only mild skin damage, irritation or inflammation of the skin, the dose may be adjusted to lower maintenance levels.

The treatment compositions providing skin protection and enhanced repair of the present invention, including pharmaceutical compositions, may be incorporated onto the topsheet 22 of the articles of the present invention and be administered alone or as combination or adjunct therapy or prophylaxis. For example, the treatment compositions can be used in combination with other skin protective factors or those found to improve other aspects of protection or healing such as the lotion formulations described above. In this manner a synergistic effect may be attained that yields a clinical efficacy greater than that realized with any single factor.

Further, while the treatment compositions described herein stimulate a spectrum of skin protective processes, skin can differ considerably in its properties, leading one to utilize a combination of a composition described-herein and another compound or factor.

Factors with reported healing properties which can be included with the silk protein compositions for use in protective/healing formulations and methods of the present invention include, for example, epidermal growth factor, fibroblast growth factor, nerve growth factor, transforming growth factors, angiogenic growth factors, heparin, fibronectin, fibrin, platelet-derived growth factor, enzymatic superoxide dismutase, extracts of blood or factors from the blood, and other similar factors.

The treatment compositions may be added to the topsheet 22 by conventional means such as spraying, coating, dipping and the like although the use of high solids spray is advantageous in cases where drying and/or compression is desired to be minimized. The amount of the treatment composition used will depend on the particular end use as well as factors such as basis weight and porosity of the substrate.

A unique and surprising aspect of the treatment compositions of the present invention includes their ability to be transferred from the topsheet to the skin. It has been found that when a liquid is introduced to the topsheet, the treatment composition will dissolve in the liquid, and then liquid-mediated transfer of the treatment composition to the skin occurs. In other words, the treatment composition including the skin health benefit agent dissolves off of the substrate into the liquid, which then deposits the thin, tenacious and substantially continuous film of the skin health benefit agent onto the skin. Urine is an example of a liquid that can transfer the treatment composition from the topsheet 22 to the skin. As another example, the liquid generated by the body after abrasion or injury to the skin, might provide sufficient liquid-mediated transfer of the treatment composition from the topsheet. In general, when wetness increases, the treatment composition will transfer from the topsheet to the skin to form a protective barrier.

The absorbent body 24 of the diaper 10, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent body 24 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. Alternatively, the absorbent body 24 may comprise a laminate of fibrous webs and superabsorbent material or other suitable means of maintaining a superabsorbent material in a localized area.

The absorbent body 24 may have any of a number of shapes. For example, the absorbent core may be rectangular, I-shaped, or T-shaped. It is generally preferred that the absorbent body 24 be narrower in the intermediate section than in the front or rear waist sections of the diaper 10. The absorbent body 24 may be provided by a single layer or, in the alternative, may be provided by multiple layers, all of which need not extend the entire length and width of the absorbent body 24. In a particular aspect of the invention, the absorbent body 24 can be generally T-shaped with the laterally extending cross-bar of the "T" generally corresponding to the front waist section 12 of the absorbent article for improved performance, especially for male infants. In the illustrated embodiments, for example, the absorbent body 24 across the front waist section 12 of the article has a cross-directional width of about 18 centimeters, the narrowest portion of the intermediate section 16 has a width of about 7.5 centimeters and in the rear waist section 14 has a width of about 11.4 centimeters.

The size and the absorbent capacity of absorbent body 24 should be compatible with the size of the intended wearer and the liquid loading imparted by the intended use of the absorbent article. Further, the size and the absorbent capacity of the absorbent body 24 can be varied to accommodate wearers ranging from infants through adults. In addition, it has been found that with the present invention, the densities and/or basis weights of the absorbent body 24 can be varied. In a particular aspect of the invention, the absorbent body 24 has an absorbent capacity of at least about 300 grams of synthetic urine.

In embodiments wherein the absorbent body 24 includes the combination of hydrophilic fibers and high-absorbency particles, the hydrophilic fibers and high-absorbency particles can form an average basis weight for the absorbent body 24 which is within the range of about 400–900 grams per square meter. In certain aspects of the invention, the average composite basis weight of such an absorbent body 24 is within the range of about 500–800 grams per square meter, and preferably is within the range of about 550–750 grams per square meter to provide the desired performance.

To provide the desired thinness dimension to the various configurations of the absorbent article of the invention, the absorbent body 24 can be configured with a bulk thickness which is not more than about 0.6 centimeters. Preferably, the bulk thickness is not more than about 0.53 centimeters, and more preferably is not more than about 0.5 centimeters to provide improved benefits. The bulk thickness is determined under a restraining pressure of 0.2 psi (1.38 kPa).

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-lefins, poly(vinyl pyrrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. In general, the high absorbency material is present in the absorbent body in an amount of from about 5 to about 90 weight percent, desirably in an amount of at least about 30 weight percent, and even more desirably in an amount of at least about 50 weight percent based on a total weight of the absorbent body 24. For example, in a particular embodiment, the absorbent body 24 may comprise a laminate which includes at least about 50 weight percent and desirably at least about 70 weight percent of high-absorbency material overwrapped by a fibrous web or other suitable means of maintaining the high-absorbency material in a localized area.

An example of high-absorbency material suitable for use in the present invention is SANWET IM 3900 polymer available from Hoechst Celanese, a business having offices in Portsmouth, Va. Other suitable superabsorbents may include FAVOR SXM 880 polymer obtained from Stockhausen, a business having offices in Greensboro, N.C.

Optionally, a substantially hydrophilic tissue wrapsheet (not illustrated) may be employed to help maintain the integrity of the structure of the absorbent body 24. The tissue wrapsheet is typically placed about the absorbent body over at least the two major facing surfaces thereof and composed of an absorbent cellulosic material, such as creped wadding or a high wet-strength tissue. In one aspect of the invention, the tissue wrap can be configured to provide a wicking layer which helps to rapidly distribute liquid over the mass of absorbent fibers comprising the absorbent body.

The absorbent body 24 of the different aspects of the present invention further includes a plurality of zones of high air permeability which allow air and vapors to readily pass through the absorbent body 24 and through the vapor permeable backsheet 20 out of the diaper 10 into ambient air. For example, as representatively illustrated in FIGS. 1 and 2, the absorbent body 24 may include a plurality of air passageways 40 which provide the absorbent body 24 with the zones or regions of high air permeability 42. In the illustrated embodiment, the portions of the absorbent body 24 adjacent the air passageways 40 provide zones or regions of high absorption 44. The zones of high air permeability 42 are designed to provide the maximum air exchange from the absorbent body 24 while the zones of high absorption 44 are designed to receive and hold the majority of the body exudates. The absorbent body 24 may define any number of zones of high air permeability 42 which provides the improved air exchange. Desirably, the absorbent body 24 defines at least 3 and more desirably at least 5 different zones of high air permeability 42 for improved performance.

The zones of high air permeability 42, such as the air passageways 40 as representatively illustrated in FIGS. 1 and 2, are configured to enhance the breathability of the article to reduce the hydration of the wearer's skin during use without allowing excessive condensation of vapor, such as urine, on the garment facing surface of the backsheet 20. Such condensation of vapor on the outer surface of the diaper 10 can undesirably dampen the wearer's clothes The zones of high air permeability 42 are generally located in the area of the diaper over which air and vapor can transfer from the topsheet 22, through the absorbent body 24 and any other intervening layer or layers of material, and out the vapor permeable backsheet 20. For example, the zones of high air permeability 42 may be located throughout the entire absorbent body 24 or may be selectively located in those regions of the absorbent body 24 which provide the maximum air exchange, such as the intermediate section 16 of the diaper 20. In a particular embodiment, the zones of high air permeability 42 are located in the front and intermediate sections 12 and 16, respectively, of the diaper 10 for improved air exchange.

The zones of high absorption 44, on the other hand, are not designed to transfer a high level of air and vapor from the interior of the diaper. Thus, the air exchange from the topsheet 22 of the diaper 10 to the backsheet 20 of the diaper and into the ambient atmosphere (exterior of the diaper) occurs generally through the absorbent body 24 in the zones of high air permeability 42. Some air exchange through the absorbent body 24 can also occur in the zones of high absorption 44 to a limited degree.

The zones of high air permeability may have any desired configuration including rectangular, circular, hourglass, oval, and the like, and may also include selected longitudinal or lateral strips or multiple regions which may be intermittently located. For example, in FIGS. 1 and 2, the zones of high air permeability 42 are provided by a plurality of air passageways 40 or apertures through the absorbent body 24 which have a generally circular configuration. In such a configuration, the zones of high absorption 44 comprise the non-apertured portions of the absorbent body 24 between the air passageways 40.

The zones of high air permeability 42 may have any desired dimensions which effectively provide improved air exchange while preventing excessive condensation of vapor from the absorbent body 24 through and onto the garment facing surface of the backsheet 20. Desirably, the zones of high air permeability 42 may define a total area of from about 5 to about 75 percent, more desirably at least about 10 percent, even more desirably from about 10 to about 70 percent, and still more desirably from about 10 to about 60 percent of the total surface area of the absorbent body 24 of the diaper 10. For example, in a diaper intended for use on a medium sized infant, the zones of high air permeability 42 may define a total area of from about 6 to about 90 square centimeters.

When the total area of the zones of high air permeability 42 is greater than the above amounts, the diaper 10 may exhibit an undesirable amount of condensation of vapor on the exposed, garment facing surface of the backsheet 20 undesirably resulting in a clammy feeling on the outer surface of the diaper. Whereas, when the total area of the zones of high air permeability 42 is less than the above amounts, the diaper 10 may exhibit a low level of air exchange resulting in high levels of skin hydration which can undesirably lead to skin irritation and rash.

The zones of high air permeability 42 of the absorbent body 24 of the diaper 10, as representatively illustrated in FIGS. 1 and 2, are constructed to be substantially permeable to at least air and preferably permeable to water vapor. For example, the zones of high air permeability 42 of the absorbent body 24 define a Frazier Porosity value which is at least about 10 percent, more desirably at least about 20 percent and even more desirably at least about 50 percent greater than the Frazier Porosity value of the zones of high absorption 44 of the absorbent body 24. As used herein, the term "Frazier Porosity" refers to the value determined according to the Frazier Porosity Test set forth below. When the zones of high air permeability exhibit Frazier Porosity values less than those indicated above, the diaper 10 may exhibit a low level of air exchange resulting in high levels of skin hydration which can undesirably lead to skin irritation and rash.

The zones of high air permeability may be provided in a variety of ways. The zones of high air permeability 42 may be integral portions of the absorbent body 24 of the absorbent article or may be provided by apertures, holes or open spaces in the absorbent body 24. For example, portions of the absorbent body 24 may be discontinuous or removed to provide the zones 42. Alternatively, the zones of high air permeability 42 may be provided by portions of the absorbent body 24 which are constructed to absorb less fluid exudates thereby resulting in improved air flow through such portions in use. For example, portions of the absorbent body 24 may be void of or contain substantially less high-absorbency material than other portions of the absorbent body 24 to provide such improved air flow. Portions of the absorbent body 24 may otherwise be treated or coated with a solution which renders them hydrophobic to provide the zones of high air permeability 42 in selected areas. In other alternative configurations, the zones of high air permeability 42 may be provided by creating voids or holes in the absorbent body 24 and placing other materials having a higher air permeability than the absorbent body 24, such as those materials described below as being suitable for the surge management layer 34, in the holes or voids.

Examples of several configurations of the absorbent body 24 according to different aspects of the present invention are representatively illustrated in FIGS. 1–6. For example, in FIGS. 1 and 2, the zones of high air permeability 42 in the absorbent body 24 are provided by a plurality of air passageways 40 or apertures through the absorbent body 24. In the illustrated embodiment, the air passageways 40 are intermittently positioned along the entire length and width of the absorbent body 24. The illustrated air passageways 40 are circular and define a diameter of about 1.27 centimeters and a total open area of about 12 percent of a total surface area of the absorbent body 24.

Figure 3:
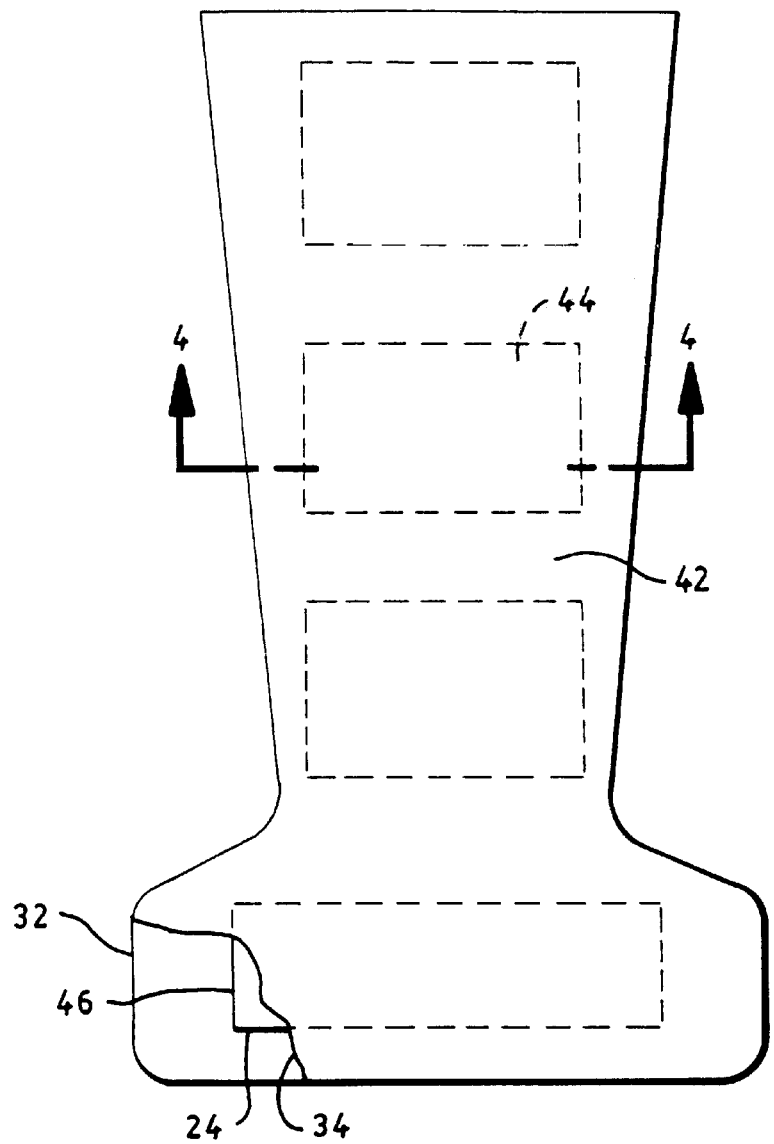
FIG. 3 representatively shows a partially cutaway, top plan view of an absorbent body for an absorbent article according to another embodiment of the invention.
Figure 4:
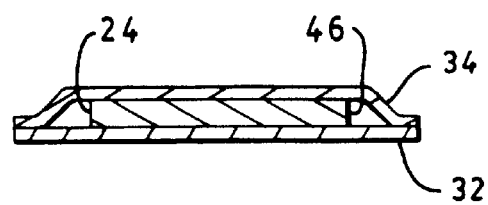
FIG. 4 representatively shows a sectional view of the absorbent body of FIG. 3 taken along line 4—4.

In FIGS. 3 and 4, the absorbent body 24 is in the form of discrete segments 46 which are spaced apart along the longitudinal direction 36 of the diaper 10. In such a configuration, the zones of high air permeability 42 are provided by the spaces between the discrete segments 46 of the absorbent body 24. The absorbent body 24 may include any number of segments 46 having a variety of shapes and sizes. For example, in the illustrated embodiment, the absorbent body 24 includes four different segments 46 spaced apart in the longitudinal direction 36 of the diaper 10. The illustrated segments 46 are generally rectangular in shape and define a width which is less than a width of the absorbent body 24 which, in the illustrated embodiment, is defined by the width of the surge management layer 34 and the ventilation layer 32 as described below. Alternatively, the segments 46 may define a width which is substantially equal to a width of the absorbent body 24. To assist in maintaining the segments 46 in the spaced apart relationship, the segments 46 can be contained between two sheets of material such as wrapsheet (not shown) or the surge management layer 34 and the ventilation layer 32. In the illustrated embodiment, the segments 46 include a laminate of high-absorbency material between two sheets or layers of material and the zones of high air permeability 42 provided by the spaces between the segments 46 define an open area of about 40 percent of a total surface are of the absorbent body 24.

Figure 5:
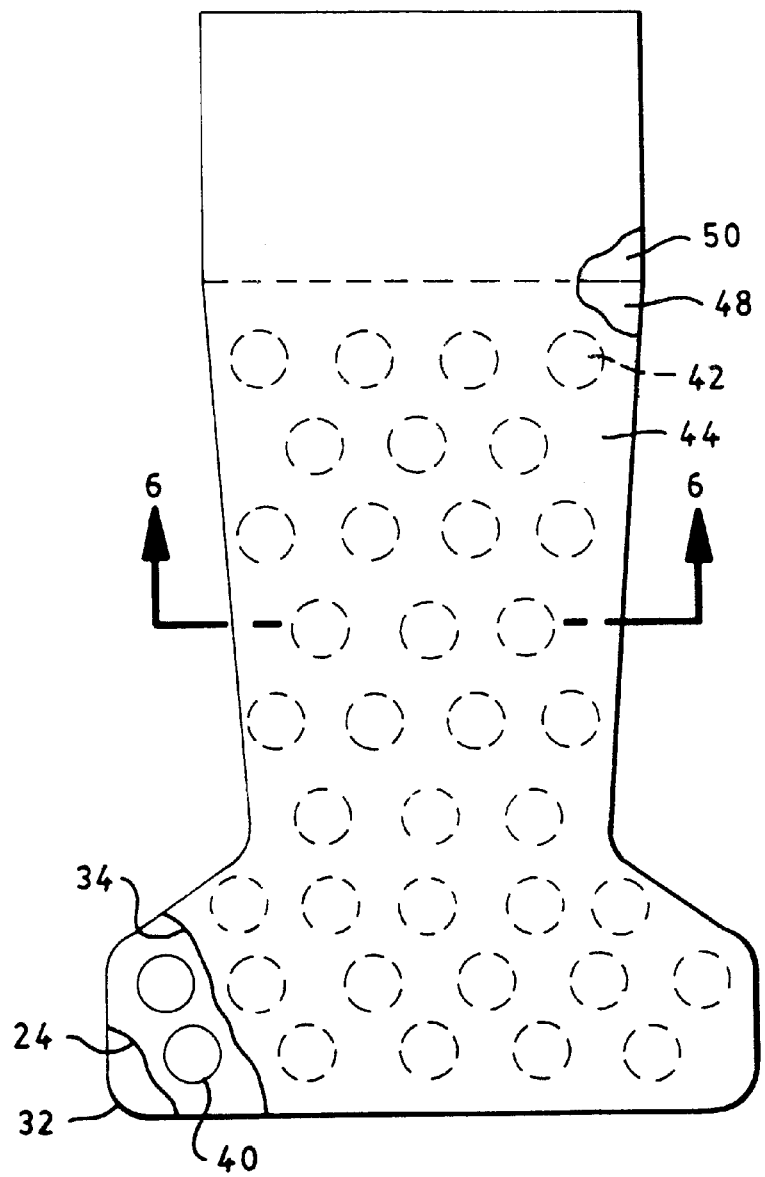
FIG. 5 representatively shows a partially cutaway, top plan view of an absorbent body for an absorbent article according to another embodiment of the invention.
Figure 6:
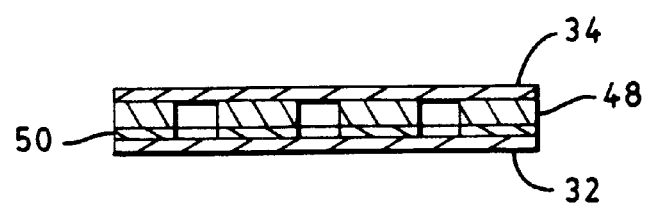
FIG. 6 representatively shows a sectional view of the absorbent body of FIG. 5 taken along line 6—6.

In FIGS. 5 and 6, the zones of high air permeability 42 in the absorbent body 24 are provided by a plurality of air passageways 40 or apertures through the absorbent body 24 similar to the embodiment illustrated in FIGS. 1 and 2. However, in the embodiment illustrated in FIGS. 5 and 6, the air passageways 40 are located in the absorbent body 24 in the front waist section 12 and the intermediate section 16 of the diaper 10 and not in the rear waist section 14. Moreover, in the embodiment illustrated in FIGS. 5 and 6, the absorbent body 24 includes an upper layer 48 and a lower layer 50 with the upper layer 48 extending only along a portion of the length of the absorbent body 24. In such a configuration, the majority of the absorbent body 24 can be located in the front waist and intermediate sections 12 and 16 of the diaper 10 for improved absorption and reduced cost. The illustrated air passageways 40 are circular and define a diameter of about 1.27 centimeters and a total open area of about 12 percent of a total surface area of the absorbent body 24.

Due to the thinness of absorbent body 24 and the high absorbency material within the absorbent body 24, the liquid uptake rates of the absorbent body 24, by itself, may be too low, or may not be adequately sustained over multiple insults of liquid into the absorbent body 24. To improve the overall liquid uptake and air exchange, the diaper of the different aspects of the present invention may further include a porous, liquid-permeable layer of surge management material 34, as representatively illustrated in FIGS. 1 and 2. The surge management layer 34 is typically less hydrophilic than the absorbent body 24, and has an operable level of density and basis weight to quickly collect and temporarily hold liquid surges, to transport the liquid from its initial entrance point and to substantially completely release the liquid to other parts of the absorbent body 24. This configuration can help prevent the liquid from pooling and collecting on the portion of the absorbent garment positioned against the wearer's skin, thereby reducing the feeling of wetness by the wearer. The structure of the surge management layer 34 also generally enhances the air exchange within the diaper 10.

Various woven and nonwoven fabrics can be used to construct the surge management layer 34. For example, the surge management layer 34 may be a layer composed of a meltblown or spunbonded web of synthetic fibers, such as polyolefin fibers. The surge management layer 34 may also be a bonded-carded-web or an airlaid web composed of natural and synthetic fibers. The bonded-carded-web may, for example, be a thermally bonded web which is bonded using low melt binder fibers, powder or adhesive. The webs can optionally include a mixture of different fibers. The surge management layer 34 may be composed of a substantially hydrophobic material, and the hydrophobic material may optionally be treated with a surfactant or otherwise processed to impart a desired level of wettability and hydrophilicity. In a particular embodiment, the surge management layer 34 includes a hydrophobic, nonwoven material having a basis weight of from about 30 to about 120 grams per square meter.

For example, in a particular embodiment, the surge management layer 34 may comprise a bonded-carded-web, nonwoven fabric which includes bicomponent fibers and which defines an overall basis weight of about 83 grams per square meter. The surge management layer 34 in such a configuration can be a homogeneous blend composed of about 60 weight percent polyethylene/polyester (PE/PET), sheath-core bicomponent fibers which have a fiber denier of about 3 d and about 40 weight percent single component polyester fibers which have a fiber denier of about 6 d and which have fiber lengths of from about 3.8 to about 5.08 centimeters.

In the illustrated embodiments, the surge management layer 34 is arranged in a direct, contacting liquid communication with the absorbent body 24. The surge management layer 34 may be operably connected to the topsheet 22 with a conventional pattern of adhesive, such as a swirl adhesive pattern. In addition, the surge management layer 34 may be operably connected to the absorbent body 24 with a conventional pattern of adhesive. The amount of adhesive add-on should be sufficient to provide the desired levels of bonding, but should be low enough to avoid excessively restricting the movement of liquid from the topsheet 22, through the surge management layer 34 and into the absorbent body 24.

The absorbent body 24 is positioned in liquid communication with surge management layer 34 to receive liquids released from the surge management layer, and to hold and store the liquid. In the shown embodiments, the surge management layer 34 comprises a separate layer which is positioned over another, separate layer comprising the absorbent body 24, thereby forming a dual-layer arrangement. The surge management layer 34 serves to quickly collect and temporarily hold discharged liquids, to transport such liquids from the point of initial contact and spread the liquid to other parts of the surge management layer 34, and then to substantially completely release such liquids into the layer or layers comprising the absorbent body 24.

The surge management layer 34 can be of any desired shape. Suitable shapes include for example, circular, rectangular, triangular, trapezoidal, oblong, dog-boned, hourglass-shaped, or oval. In certain embodiments, for example, the surge management layer can be generally rectangular-shaped. In the illustrated embodiments, the surge management layer 34 is coextensive with the absorbent body 24. Alternatively, the surge management layer 34 may extend over only a part of the absorbent body 24. Where the surge management layer 34 extends only partially along the length of the absorbent body 24, the surge management layer 34 may be selectively positioned anywhere along the absorbent body 24. For example, the surge management layer 34 may function more efficiently when it is offset toward the front waist section 12 of the garment. The surge management layer 34 may also be approximately centered about the longitudinal center line of the absorbent body 24.

Additional materials suitable for the surge management layer 34 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

As representatively illustrated in FIGS. 1 and 2, the diaper 10 may also include a ventilation layer 32 located between the backsheet 20 and the absorbent body 24. The ventilation layer 32 serves to facilitate the movement of air within and through the diaper 10 and prevent the backsheet 20 from being in surface to surface contact with at least a portion of the absorbent body 24. Specifically, the ventilation layer 32 serves as a conduit through which air and water vapor can move from the absorbent body 24 through the vapor permeable backsheet 20.

The ventilation layer 32 may be formed from materials described above as being suitable for the surge management layer 34 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material or a composite of two or more layers of material. In a particular embodiment, the ventilation layer 32 includes a hydrophobic, nonwoven material having a thickness of at least about 0.10 centimeters determined under a restraining pressure of 0.05 psi (0.34 kPa) and a basis weight of from about 20 to about 120 grams per square meter. For example, the ventilation layer 32 may comprise a bonded-carded-web, nonwoven fabric which includes bicomponent fibers and which defines an overall basis weight of about 83 grams per square meter. The ventilation layer 32 in such a configuration can be a homogeneous blend composed of about 60 weight percent polyethylene/polyester (PE/PET), sheath-core bicomponent fibers which have a fiber denier of about 3 d and about 40 weight percent single component polyester fibers which have a fiber denier of about 6 d and which have fiber lengths of from about 3.8 to about 5.08 centimeters.

The ventilation layer 32 can be of any desired shape. Suitable shapes include for example, circular, rectangular, triangular, trapezoidal, oblong, dog-boned, hourglass-shaped, or oval. The ventilation layer 32 may extend beyond, completely over or partially over the absorbent body 24. For example, the ventilation layer 32 may suitably be located over the intermediate section 16 of the diaper 10 and be substantially centered side-to-side with respect to the longitudinal centerline 36 of the diaper 10. It is generally desired that the entire absorbent body 24 be overlaid with the ventilation layer 32 to prevent substantially all surface to surface contact between the backsheet 20 and the absorbent body 24. In the illustrated embodiments, the ventilation layer 32 is coextensive with the absorbent body 24. This allows for the maximum degree of air exchange with minimal dampness on the garment facing surface of the backsheet 20.

In the illustrated embodiments, the ventilation layer 32 is arranged in a direct, contacting liquid communication with the absorbent body 24. The ventilation layer 32 may be operably connected to the backsheet 20 with a conventional pattern of adhesive, such as a swirl adhesive pattern. In addition, the ventilation layer 32 may be operably connected to the absorbent body 24 with a conventional pattern of adhesive. The amount of adhesive add-on should be sufficient to provide the desired levels of bonding, but should be low enough to avoid excessively restricting the movement of air and vapor from the absorbent body 24 and through the backsheet 20.

The ventilation layer 32 may further serve to quickly collect and temporarily hold discharged liquids, which pass through the absorbent body 24 and, in particular, through the zones of high air permeability 42 within the absorbent body 24. The ventilation layer 32 may then transport such liquids from the point of initial contact and spread the liquid to other parts of the ventilation layer 32, and then substantially completely release such liquids into the layer or layers comprising the absorbent body 24.

The different article embodiments of the present invention, as representatively illustrated in FIGS. 1–6, advantageously provide improved absorbent articles which exhibit substantially reduced levels of hydration of the wearer's skin when in use compared to conventional absorbent articles. In particular, the reduced levels of skin hydration promote drier, more comfortable skin and render the skin less susceptible to the viability of microorganisms. Thus, wearer's of absorbent articles made according to the present invention have reduced skin hydration which can lead to a reduction in the incidence of skin irritation and rash.

Moreover, the combination of the highly breathable articles of the present invention with the lotion formulations and/or treatment compositions of the present invention can provide a synergistic reduction in the incidence of skin irritation and rash. In particular, the lotion formulations and treatment compositions can provide a skin barrier and anti-inflammatory function. Thus, the absorbent articles made according to the present invention can maintain or improve the health of the wearer's skin.

TEST PROCEDURES

Hydrostatic Pressure Test

The Hydrostatic Pressure Test is a measure of the liquid barrier properties of a material. In general, the Hydrostatic Pressure Test determines the height of water (in centimeters) in a column which the material will support before a predetermined amount of water passes through. A material with a higher hydrohead value indicates it is a greater barrier to liquid penetration than a material having a lower hydrohead value. The Hydrostatic Pressure Test is performed according to Method 5514—Federal Test Methods Standard No. 191A.

Frazier Porosity Test

The Frazier Porosity values referred to in the present specification can be determined employing a Frazier Air Permeability Tester (Frazier Precision Instrument Co., Gaithersburg, Md.) and Method 5450, Federal Test Methods Standard No. 191A. For the purposes of the present invention, the test is conducted with a sample which measures 8 inches×8 inches.

Water Vapor Transmission Test

A suitable technique for determining the WVTR (water vapor transmission rate) value of a material is as follows.

For the purposes of the present invention, 3-inch diameter (76 millimeter) circular samples are cut from the test material and from a control material, Celguard® 2500 (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test WVTR} = \frac{[(\text{grams weight loss over 24 hours}) \times 7571]}{24} \, (\text{g/m}^2/24 \text{ hours})$$

The relative humidity within the oven is not specifically controlled. Under predetermined set conditions of 100° F. and ambient relative humidity, the WVTR for Celguard 2500 has been determined to be 5000 g/m$^2$/24 hours. Accordingly, Celguard 2500 is run as a control sample with each test. Celguard 2500 is a 0.0025 cm thick film composed of a microporous polypropylene.

Skin Hydration Test

Skin hydration values are determined by measuring total evaporative water loss (EL) and can be determined by employing the following test procedure.

The test is conducted on partially toilet trained infants who have no lotions or ointments on the skin and have not been bathed within 2 hours prior to the test. Each infant tests one diaper during each test session. The test diapers include a test code and a control code. The test diapers (test code and control code) are randomized.

Each test diaper is weighed before and after use to verify the volume of liquid added into the diaper. A felt tip pen is employed to mark an "X" at the target zone inside the diaper, with the "X" positioned 6.5 inches below the top front edge of the diaper and centered side-to-side. The EL measurements are taken with an evaporimeter, such as an Evaporimeter EP1 instrument distributed by Servomed AB, Stockholm, Sweden. Each test measurement is taken over a period of two minutes with EWL values taken once per second (a total of 120 EWL values). The digital output from the Evaporimeter EP1 instrument gives the rate of evaporative water loss (EWL) in g/m$^2$/hr. Skin hydration values (SHV) are in units of total amount of water loss per unit area measured during the Two-minute sampling period and are calculated as follows.

$$SHV\ (g/m^2/hour) = \frac{\sum_{n=1}^{120}(EWL)_n}{120}$$

A preliminary skin hydration value measurement is taken after a 15-minute "dryout" period when the infant wears only a long T-shirt or dress and is in the supine position. The measurement is taken on the infant's lower abdomen, in a region corresponding to the target zone of the diaper, using the evaporimeter for the purpose of establishing the initial skin hydration value of the infant's skin at the diaper target zone. If the preliminary SHV is less than 10 g/m²/hour, a diaper is then placed on the infant. If the preliminary SHV is greater than 10 g/m²/hour, the "dryout" period is extended until a reading below 10 g/m²/hour is obtained. Prior to securing the diaper on the infant, a tube is positioned to direct a flow of liquid to hit the premarked target zone. Once the diaper is secured, 210 milliliters of adjusted 0.9 weight percent aqueous saline is added in three insults of 70 milliliters each at a rate of 15 milliliters/second with a 45 second delay between insults.

The infant wears the diaper for 60 minutes after which the diaper is removed and a test measurement of skin hydration is taken on the lower abdomen corresponding to the target zone mark of the diaper. The measurement is taken over a 2-minute period. The used diaper is then weighed. Relative humidity and temperature measurements can be taken within the diaper prior to the skin hydration measurements being taken. The test procedure is then repeated the next day for each infant using the diaper type (test or control) which the infant has not yet worn. The control diaper provides a standardized basis for comparing the performance of the diaper configuration being tested and evaluated. The control diapers used in the tests performed in connection with the Examples were commercially available HUGGIES® Supreme diapers sold by Kimberly-Clark Corporation.

Data is discarded for any infants which have added to the loading of saline solution. The value reported for the mean net SHV (grams/ml in one hour) is the arithmetic mean for all infants of the post-wear skin hydration value, taken at the lower abdomen (target zone mark), minus the skin hydration value measured at the lower abdomen prior to placing the diaper on the infant (after "dryout" period). A separate mean net SHV is determined for the test code diapers and the control code diapers.

The net skin hydration value is determined as follows:

Net SHV=Y−Z

Where:
Y=skin hydration value measured at target zone mark of an individual infant
Z=baseline skin hydration value measured on the lower abdomen after "dryout" period prior to placing diaper on the infant
$SHV_1$=skin hydration value for individual infant
Then, $$\text{Mean Net } SHV = \frac{\sum_{i=1}^{N} \text{Net } SHV_i}{N}$$

Where: N=number of infants in study

The percent reduction in skin hydration is determined as follows:

$$\%\,\text{Reduction} = \frac{\sum_{i=1}^{N}[((C-D)/C)\times 100]}{N}$$

Where:
C=Net $SHV_1$ for control diaper code
D=Net $SHV_1$ for test diaper code
N=number of infants in study Tracer Gas Test The Tracer Gas Test is a measure of the rate of air exchange in garments such as absorbent articles and is a steady flow/steady state test described generally in *TAPPI JOURNAL.*, Volume 80, No. 9, Sep. 1997. In general, the air exchange rate values are calculated from the measured mass exchange within the garment. The test involves injecting a tracer gas at a constant rate inside the article next to the outer surface of the torso of a mannequin while the article is secured about the mannequin. Simultaneously, the concentration of the tracer gas in the air space between the article and the mannequin is measured by withdrawing a sample at the same constant rate as the injection. The air exchange rate is then be determined based on mass balances of the tracer gas and the air within the space in question. The Tracer Gas Test is completed as follows:

Equipment

1. Mannequin—The test is conducted with Step 3 or Step 4 sized diapers designed for infants weighing from about 16 to about 28 pounds and from about 22 to about 37 pounds, respectively. The diapers are placed on mannequins which have the following dimensions:

| Step 3 | |
|---|---|
| height (waist to knees) | 26 centimeters |
| circumference at waist | 42 centimeters |
| circumference at hips | 44 centimeters |
| thigh circumference | 22 centimeters |
| Step 4 | |
| height (waist to knees) | 28 centimeters |
| circumference at waist | 48 centimeters |
| circumference at hips | 51 centimeters |
| thigh circumference | 27 centimeters |

2. A test area which is environmentally controlled to 20° C. and 50% relative humidity.

3. $CO_2$ Analyzer—An infrared $CO_2$ Analyzer such as Model 17515A commercially available from Vacu-Med Vacumetrics, 4483 McGrath Street #102, Ventura, Calif.

4. Rotameters—Rotameters to maintain gas flow rates such as Matheson Rotameter Model TS-35 commercially available from Specialty Gases Southeast Inc., 3496 Peachtree Parkway, Suwanee, Ga.

5. Gas Cylinders—Two gas cylinders of calibrated medical grade gas at a pressure of 4 kPa from Specialty Gases Southeast Inc., 3496 Peachtree Parkway, Suwanee, Ga. The tracer gas includes 5% $CO_2$ and air and the calibration gas is 100% air.

Procedure

1. Turn the $CO_2$ analyzer on. After it has been on for 30 minutes, calibrate the analyzer with the calibration gas and adjust the flow control to achieve a flow rate of 150 cubic centimeters per minute through the analyzer.

2. Place the diaper to be tested on the mannequin.

3. Turn on the $CO_2$ tracer gas flow. The flow rate of the injected tracer gas into the space between the diaper and the mannequin must be equal to the sample flow rate through the $CO_2$ analyzer (150 cc/min.).

4. Measure and record the concentration (C) of the tracer gas ($CO_2$) in the air space between the diaper and the mannequin every 10 seconds for 20 minutes. The data over the last 10 minutes are averaged and used to calculate the air exchange rate as follows:

Air Exchange Rate=150 cc/min *[$(C_T-C)/(C-C_o)$]

wherein, $C_T$=concentration of the tracer gas (5%)

C=concentration of the tracer gas in the space being measured $C_o$=concentration of the tracer gas in the chamber environment (0.04%)

The Dry Air Exchange Rate is the air exchange rate as determined according to the above procedure before the diaper has been subjected to any insults. The Wet Air Exchange Rate is the air exchange rate determined according to the above procedure except that once the diaper is secured to the mannequin, 180 milliliters (Step 3) or 210 milliliters (Step 4) of adjusted 0.9 weight percent aqueous saline is added in three insults of 60 or 70 milliliters each at a rate of 15 milliliters/second with a 45 second delay between insults. The Wet Air Exchange Rate/Dry Air Exchange Rate ratio is determined by dividing the Wet Air Exchange Rate by the Dry Air Exchange Rate for the same sample.

C. albicans Viability Test

The C. albicans Viability Test is a measure of the effect of absorbent garments, such as disposable diapers, on the viability of pathogenic microorganisms and, in particular, Candida albicans. In general, the C. albicans Viability Test involves inoculating delineated sites of each volar forearm of test subjects with a known suspension of C. albicans cells, covering the sites with full thickness patch from the absorbent garment, and determining the viability after a 24 hour period.

A full thickness test sample patch having a length of about 5 centimeters and a width of about 5 centimeters is cut from the target zone of each product to be tested. The target zone is generally that portion of the product intended to receive urine discharge from the wearer and typically includes portions of the intermediate and front waist sections of the product somewhat forward of the lateral centerline of the product. In a typical diaper configuration, the full thickness test sample patch includes the topsheet, absorbent body, backsheet and any intervening layers. Approximately 15 milliliters of a 0.9 weight percent saline solution is added to the test sample patch and allowed to soak in for 2 minutes before the samples are placed on the forearms of the test subjects. A test site area of about 6.15 square centimeters is marked on each of the test subject's volar forearms. Approximately 0.01 milliliters of a 0.9 weight percent saline solution containing a known suspension of C. albicans cells is delivered to the test site with micropipettes and the suspension is then spread uniformly across the test site. After air drying, the test site is covered with the test sample patch which is secured in position using adhesive tape completely surrounding the sample.

After 24 hours, the test sample patches are removed and a quantitative culture is obtained from the test site using the detergent scrub method set forth in "A New Method For Quantitative Investigation of Cutaneous Bacteria", P. Williamson and A. M. Klingman, *Journal of Investigative Dermatology*, 45:498–503, 1965, the disclosure of which is hereby incorporated by reference. Briefly, a sterile glass cylinder encompassing an area of 6.15 square centimeters is centered over the test site and held firmly to the skin. One milliliter of 0.1 weight percent Triton-x-100 in 0.075M phosphate buffer having a pH of 7.9 is pipetted into the glass cylinder and the area scrubbed for one minute using a sterile Teflon rod. The fluid is aspirated with a sterile pipette and a second milliliter of 0.1 weight percent Triton-x-100 in 0.075M phosphate buffer having a pH of 7.9 is added to the glass cylinder. The scrub step is repeated and the two washes are pooled. Each pooled sample is diluted in ten-fold steps with of 0.05 weight percent Triton-x-100 in 0.0375M phosphate buffer having a pH of 7.9. A 0.01 milliliter aliquot of each dilution is inoculated onto Sabourands agar containing antibiotics. Duplicate cultures are prepared and incubated at room temperature for 48 hours.

After incubation, the number of colony forming units are counted using standard microbiological methods. The C. albicans viability under a patch of the test sample can then be compared to the C. albicans viability under a control patch from a conventional absorbent article having a non-breathable outer cover, i.e. an outer cover having a WVTR of less than 100 grams per square meter per 24 hours, such as the diaper described below in connection with Comparative Example 4.

Skin TemDerature Test

Skin temperature values can be determined by employing the following test procedure. The test is conducted on the bare forearm of adult human beings who have no lotions, powders or ointments on the skin and have no skin disorders. The subjects also have not been bathed, swam, smoked, exercised or consumed caffeine within 2 hours prior to and during the test. Each subject tests two articles such as diapers during each test session. The test diapers may include a test code and a control code such as the code identified in Comparative Example 6. The test diapers (test code and control code) are randomized and are conventional Step 3 sized diapers, i.e. for infants weighing 16–28 pounds.

Each test diaper is weighed before and after use to verify the volume of liquid added into the diaper. A pen is employed to mark a 1"×1" square at the target zone on the inside and outside of the diaper, with the center of the square positioned 6.0 inches below the top front edge of the diaper and centered side-to-side. The temperature and humidity measurements are taken with a temperature sensor, such as a thermocouple probe with vinyl insulated 10-kt gold-plated disc sensor distributed by Cole-Parmer, a business having offices located in Vemon Hills, Ill. under the trade designation P-08506-80 which is attached to a Digi-Sense® Temperature/Humidity Logger distributed by Cole-Parmer, a business having office located in Vemon Hills, Ill. under the trade designation Model # 91090-00. The thermocouple probe is calibrated to a pre-calibrated probe (3700-52) built into the data logger. The skin temperature measurements are taken continuously once per minute.

Upon arrival, each test subject is subjected to a 15 minute acclimation period in a controlled environment at 40% relative humidity and 71° F. One temperature sensor is attached to each forearm, approximately midway between the wrist and elbow. The lead of the sensor is placed towards the elbow and the sensor is secured in place with a piece of tape such as Steri-Strip suture tape (0.25"×1.5") commercially available from 3M on top of the sensor and another piece of tape to hold the sensor lead in place. Baseline skin temperatures are recorded for a period of 5 minutes (5 minute total test time) without a diaper attached to the forearm.

The sample diapers are then attached to respective forearms of each test subject such that the 1"×1" target zones on the diaper are located over the temperature sensor. Prior to securing the diapers on the forearms of the subject, a fluid dispenser nozzle, acclimated to room temperature, is positioned in each diaper above the temperature sensor to direct a flow of liquid to hit the premarked target zone. Each diaper does not overlap at the target zone and is secured in place by fastening masking tape which fastens the upper and lower portions of the diaper together without contacting the skin of the wearer. A size 3 elastic stockinet retainer commercially available from Glenwood, Inc. is placed over the entire diaper and forearm. Once the diapers are secured, dry diaper skin temperature is recorded for 5 minutes.

The diapers are then loaded with 180 milliliters of body temperature adjusted 0.9 weight percent aqueous saline is added in three insults of 60 milliliters each at a rate of 15 milliliters/second with a 45 second delay between insults. The fluid dispenser nozzle is removed from each diaper. The subject wears each diaper for 120 additional minutes while skin temperature readings are recorded every minute. The diapers are then removed and weighed.

The value reported for the skin temperature is the arithmetic mean for all subjects at the specific time during the testing period for each sample. The Wet Skin Temperature/Dry Skin Temperature ratio is then determined by dividing the skin temperature value after 120 minutes of wearing the wetted sample (130 minute total test time) by the skin temperature value after 5 minutes of wearing the dry sample (10 minute total test time).

Z-Direction Lotion Migration Test

This test determines the quantity of lotion which remains on the target area of the bodyfacing surface of an absorbent article after a given period of time at a given temperature. Specifically, the purpose of the test is to compare the amount of lotion present in the target zone on articles stored at a lower temperature with that present on articles stored at a higher temperature. The test simulates storage at elevated temperature conditions which may occur to such artides. For example, such articles may be stored in the trunk of a vehicle or in a warehouse in a warm climate such as in a warehouse in Arizona in July or August. The z-direction migration loss is a measure of the lotion migration after storage at 130° F. when compared to the lotion migration at 73° F. after a fixed period of time. Thus, this test predicts the amount of lotion which will be available on the bodyfacing surface of the article for transfer to the skin when the article is used as well as how quickly it will undesirably migrate away from or along the bodyfacing surface of the article in use.

Specifically, the test is conducted as follows:

1. Ten (10) products having a lotion formulation applied to the topsheet or bodyside liner are obtained.

2. Five (5) products are placed in a controlled environment at a temperature of 73° F. and a relative humidity of 50% for a fixed period of time such as, for example, 28 days. The other five (5) products are placed in a controlled environment at a temperature of 130° F. and ambient humidity for the same period of time.

3. The products are removed from the controlled environment and a sample of the topsheet having a width of 3.75 inches and a length of 13 inches is removed from the center of each product.

Figure 8:
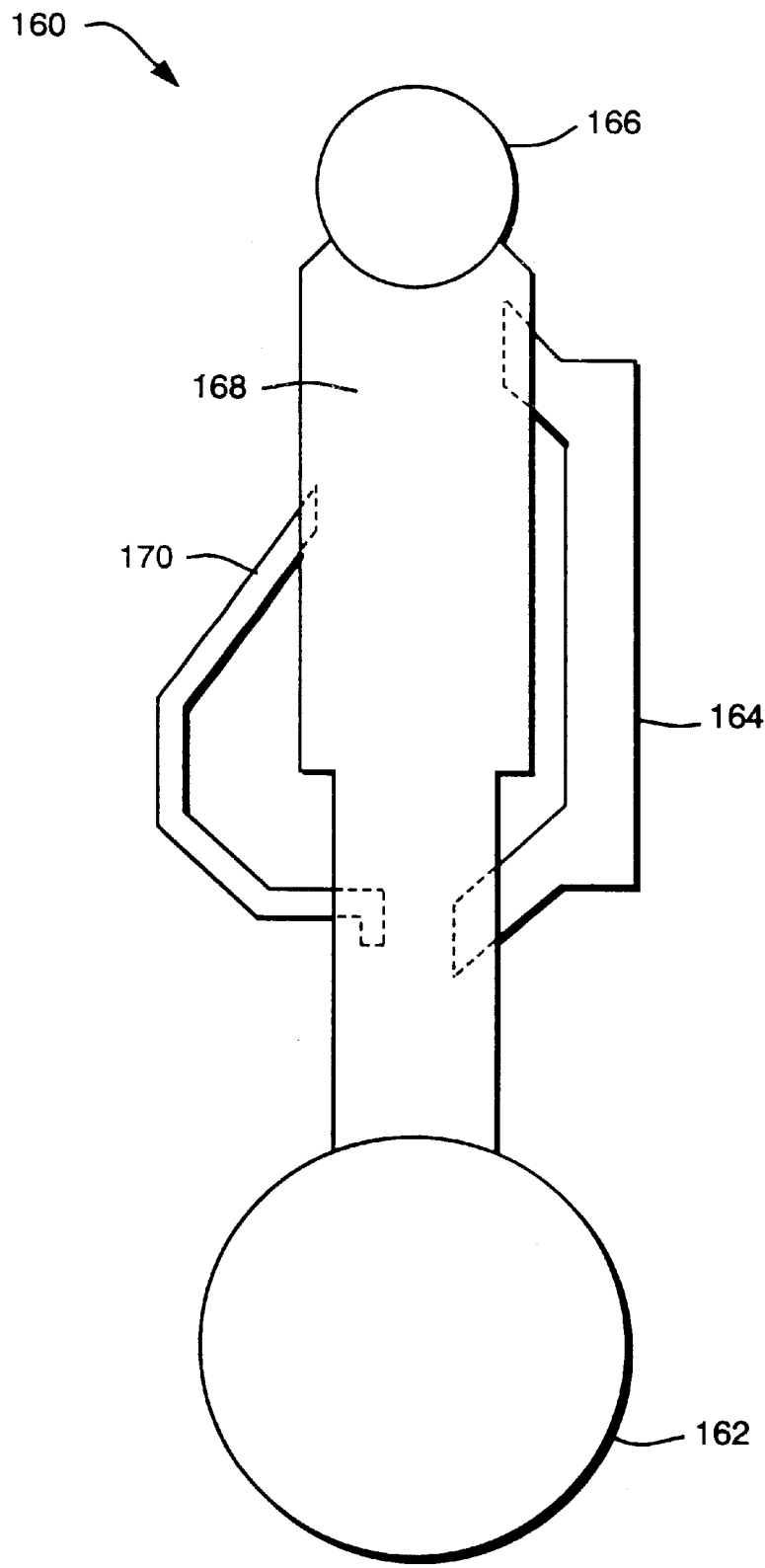
FIG. 8 representatively shows the test apparatus for the Lotion Migration Test set forth herein.

4. The samples are then subjected to Soxhlet Extracton with Gravimetric Analysis (SEGA) as follows. A SEGA test apparatus such as that representatively illustrated in FIG. 8 is used. The test apparatus 160 includes a reboiler 162, chloroform vapor duct 164, cold water condenser 166, holding tank 168 where the samples are placed and a chloroform recycle duct 170. The components of the test apparatus are conventional glassware well known to those skilled in the art. For example, the reboiler may include a 250 ml round bottom flask and the vapor duct can include an 85 ml soxlet. A sample is placed in the holding tank 168 and subjected to chloroform washing cycles for 2.5 hours. 125 milliliters of liquid chloroform is placed in the reboiler. The chloroform vaporizes and rises up through the vapor duct 164 into the condenser 166 having tap water therein which, in turn, causes the chloroform to liquefy and fall into the holding tank 168 with the sample. The chloroform dissolves the lotion from the liner sample. When the liquid chloroform reaches a high enough level, the recycle duct returns the chloroform/lotion mixture to the reboiler. The temperature in the reboiler is controlled such that it is above the boiling point of the chloroform but below that of the lotion such that only the chloroform vaporizes to start the process over again. One complete wash cycle takes approximately 15 minutes with about 75 milliliters of chloroform circulating through the liner sample in each cycle. Upon completion, the chloroform in the evaporator is evaporated utilizing a conventional vacuum evaporator such as a rotovap commercially available under the model number Buchi 011 RE 121 for a period of 4 minutes followed by placing the lotion in an aluminum pan and heating on a hot plate with forced air circulation for an additional 30 minutes.

5. The residue (lotion) remaining for each sample is then weighed. The amount of lotion recovered from the products stored at 73° F. is then compared to the amount of lotion recovered from the products stored at 130° F. to determine the stability of the lotion formulation at high temperature.

The z-direction migration loss of the absorbent article is then determined as follows:

$$\text{Z-direction migration loss } (\%) = [(L_{73} - L_{130})/L_{73}] \times 100$$

wherein, $L_{73}$=average weight (g) of lotion recovered per sample stored at 73° F.

$L_{130}$=average weight (g) of lotion recovered per sample stored at 130° F.

CD-Direction Lotion Migration Test

This test determines the quantity of lotion which remains on the specific location where it is applied on the bodyfadng surface of an absorbent article after a given period of time at a given temperature. Specifically, the purpose of the test is to compare the amount of lotion present in the applied location on the topsheet or bodyside liner with that present on the remaining portions of the topsheet of the articles after being stored at an elevated temperature. The test simulates storage at elevated temperature conditions which may occur to such articles. For example, such articles may be stored in the trunk of a vehicle or in a warehouse in a warm climate such as in a warehouse in Arizona in July or August. The cd-direction migration loss is a measure of the lateral lotion migration along the bodyfacing surface of the article after storage at 130° F. after a fixed period of time. Thus, this test predicts the amount of lotion which will be available in the desired location on the bodyfacing surface of the article for transfer to the skin when the article is used as well as how quickly it will undesirably migrate away from or along the bodyfacing surface of the article in use.

Specifically, the test is conducted as follows:

1. Five (5) products having a lotion formulation applied to the topsheet in a specific pattern are obtained.

2. The products are placed in a controlled environment at a temperature of 130° F. and ambient humidity for a fixed period of time such as, for example, 28 days.

3. The products are removed from the controlled environment and the topsheet on each product is removed and dissected to remove the portion of the topsheet to which the lotion was actually applied. For example, if the lotion was applied as 4 continuous lines having a width of 0.25 inches with spaces of 0.75 inches in between, the 4 strips of topsheet would be removed.

4. The samples which include the portions of the topsheet to which the lotion was applied are then grouped together and subjected to Soxhlet Extraction with Gravimetric Analysis (SEGA) as described above. The remaining portions of the topsheet are also grouped together and subjected to a separate SEGA extraction.

5. The residue (lotion) remaining for each group is then weighed. The amount of lotion recovered from the portions of the topsheet to which the lotion was applied is then compared to the amount of lotion recovered from the remaining portions of the topsheet to determine the stability of the lotion formulation at high temperature.

The cd-direction migration loss of the absorbent article is then determined as follows:

$$\text{CD-direction migration loss } (\%) = [L_{sp}/(L_a + L_{sp})] \times 100$$

wherein, $L_{sp}$=average weight (g) of lotion recovered from the portions of the topsheet to which the lotion was not applied per diaper $L_a$=average weight (g) of lotion recovered from the portions of the topsheet to which the lotion was applied per diaper.

The following examples are presented to provide a more detailed understanding of the invention. The specific materials and parameters are exemplary and are not intended to specifically limit the scope of the invention.

EXAMPLES

Example 1

Disposable diapers having the same general construction as the HUGGIES® Supreme Step 3 diapers described in connection with Comparative Example 2 below were hand made and tested. The diapers were substantially the same as the Supreme diapers except that the backsheet, absorbent core, surge layer and elasticized legbands of the diapers were replaced or modified and a ventilation layer was added between the backsheet and the absorbent core.

In the tested diapers, the backsheet included a microporous film/nonwoven laminate material comprising a spunbond nonwoven material laminated to a microporous film. The spunbond nonwoven comprised filaments of about 1.8 denier extruded from a copolymer of ethylene with about 3.5 weight percent propylene and defined a basis weight of from about 20 grams per square meter. The film comprised a cast coextruded film having calcium carbonate particles therein and defined a basis weight of about 58 grams per square meter prior to stretching. The film was preheated, stretched and annealed to form the micropores and then laminated to the spunbond nonwoven material. The resulting microporous film/nonwoven laminate based material had a basis weight of 45 grams per square meter and a water vapor transmission rate of about 4000 grams per square meter per 24 hours. Examples of such film/nonwoven laminate materials are described in more detail in U.S. patent application Ser. No. 08/882,712 filed Jun. 25, 1997, in the name of McCormack et al. and entitled "LOW GAUGE FILMS AND FILMINONWOVEN LAMINATES", the disclosure of which has been incorporated by reference.

The absorbent core in the tested diapers was a dual layer absorbent having the general configuration set forth in FIGS. 5 and 6 except that there were no holes or apertures through either layer of the absorbent. The absorbent core included an upper layer and a lower layer with the upper layer extending from the front edge of the absorbent core to a location about two thirds of the total length of the absorbent core. The absorbent core included from about 10 to about 11 grams of wood pulp fibers and from about 10 to about 11 grams of superabsorbent material and, accordingly, included about 50 weight percent wood pulp fibers and about 50 weight percent superabsorbent material. The lower layer had a basis weight of about 230 grams per square meter and the upper layer had a basis weight of about 560 grams per square meter to provide a total basis weight of about 790 grams per square meter in the front section of the core and a basis weight of about 230 grams per square meter in the back section of the core. The absorbent core further defined a width in the crotch section of about 6.35 centimeters.

The surge layer was located between the absorbent core and the topsheet and was the same material as the surge layer in the Supreme diapers described in Comparative Example 2 except that it was modified to be coextensive with the absorbent core. The diapers also included a ventilation layer between the absorbent core and the backsheet of the diaper. The ventilation layer was made of the same material as the surge layer and was also coextensive with the absorbent core. The diapers also included an elasticized leg band assembly along about two thirds of the length of each longitudinal side edge of the diaper. The assembly had six (6) strands of elastomeric material laminated to a breathable, nonwoven fabric layer. The elastic strands were composed of LYCRA® elastomer aligned along the longitudinal length of the diaper to elasticize and gather the diaper legbands.

Four samples of the diapers were subjected to the Tracer Gas Test set forth above. The results are set forth in Table 1 below.

Example 2

Disposable diapers having the same general construction as the diapers described in connection with Example 1 were hand made and tested. The diapers were substantially the same as the Example 1 diapers except that the absorbent body was modified to include a plurality of holes therethrough in the region where the upper layer overlaid the lower layer as illustrated in FIGS. 5 and 6. The holes had a diameter of 1.27 centimeters to provide an open area of about 12 percent based on a total surface area of the absorbent body. Four samples of the diapers were subjected to the Tracer Gas Test set forth above. The results are set forth in Table 1 below.

Example 3

Disposable diapers having the same general construction as the diapers described in connection with Example 2 were hand made and tested. The diapers were substantially the same as the Example 2 diapers except that the ventilation layer between the absorbent body and the backsheet was removed. Four samples of the diapers were subjected to the Tracer Gas Test set forth above. The results are set forth in Table 1 below.

Example 4

Disposable diapers having the same general construction as the diapers described in connection with Example 2 were hand made and tested. The diapers were substantially the same as the Example 2 diapers except that the holes in the absorbent body had a diameter of 2.54 centimeters which also defined an open are of about 12 percent of the total surface are of the absorbent body. Four samples of the diapers were subjected to the Tracer Gas Test set forth above. The results are set forth in Table 1 below.

Example 5

Disposable diapers having the same general construction as the diapers described in connection with Example 2 were hand made and tested. The diapers were substantially the same as the Example 2 diapers except that the layered absorbent body was replaced with a non-layered absorbent body which included about 62 weight percent wood pulp fibers and about 38 weight percent superabsorbent and defined a basis weight in the front section of about 750 to about 850 grams per square meter and a basis weight in the back section of about 375 to about 425 grams per square meter. Four samples of the diapers were subjected to the Tracer Gas Test set forth above. The results are set forth in Table 1 below.

Example 6

Disposable diapers having the same general construction as the diapers described in connection with Example 2 were hand made and tested. The diapers were substantially the same as the Example 2 diapers except that the dual layered absorbent core was replaced with a laminate which included about 80 weight percent superabsorbent material commercially available from Stockhausen under the trade designation FAVOR SXM 880 overwrapped by a tissue layer of cellulosic fibers having a basis weight of about 26 grams per square meter. The absorbent body also included apertures therethrough having a diameter of 1.27 centimeters to provide an open area of about 12 percent of the total surface area of the absorbent body. Four samples of the diapers were subjected to the Tracer Gas Test set forth above. The results are set forth in Table 1 below.

Example 7

Disposable diapers having the same general construction as the diapers described in connection with Example 2 were hand made and tested. The diapers were substantially the same as the Example 2 diapers except that the absorbent body was replaced with a laminate which included about 80 weight percent superabsorbent material commercially available from Stockhausen under the trade designation FAVOR SXM 880 overwrapped by a tissue layer of cellulosic fibers having a basis weight of about 26 grams per square meter. The laminate was provided in four segments as representatively illustrated in FIGS. 3 and 4 which resulted in an open area for the absorbent body of about 40 percent of a total surface area of the absorbent body. Four samples of the diapers were subjected to the Tracer Gas Test set forth above. The results are set forth in Table 1 below.

Example 8

Disposable diapers having the same general construction as the diapers described in connection with Example 2 were hand made and tested. The diapers were substantially the same as the Example 2 diapers except that the backsheet was modified to define a water vapor transmission rate of about 1870 grams per square meter per 24 hours. Four samples of the diapers were subjected to the Tracer Gas Test set forth above. The results are set forth in Table 1 below.

Comparative Example 1

Disposable diapers having the same general construction as the Supreme Step 3 diapers as described in connection with Example 2 were hand made and tested. The diapers were substantially the same as the Example 2 diapers except that the backsheet was replaced with a 1 mil thick polyethylene film material having a water vapor transmission rate of less than 100 grams per square meter per hour. Four samples of the diapers were subjected to the Tracer Gas Test set forth above. The results are set forth in Table 1 below.

Comparative Example 2

Disposable diapers having the same general construction as those diapers commercially available from Kimberly-Clark Corporation under the trade designation HUGGIES® Supreme Step 3 were tested.

In essence, the Supreme diapers comprised an absorbent core consisting of a mixture of wood pulp fibers and superabsorbent material surrounded by a two piece cellulosic wrapsheet having a basis weight of about 16–21 grams per square meter. The absorbent core included from about 12.5 to about 13.5 grams of airlaid wood pulp fibers and from about 7.0 to about 8.5 grams of superabsorbent material. The superabsorbent material was purchased from Stockhausen under the trade designation FAVOR SXM 880. The superabsorbent material was homogeneously mixed with the pulp fibers to form a unitary layer having a density within the range of 0.25 to 0.35 grams per cubic centimeter. The homogeneous mixture of the superabsorbent material and the wood pulp fibers was zoned along the machine direction to provide a basis weight of from about 600 to about 700 grams per square meter in the front section of the absorbent core and a basis weight of from about 300 to about 350 grams per square meter in the back section of the absorbent core.

The Supreme diapers further included a composite backsheet comprising a vapor-permeable barrier layer adhesively laminated to a spunbond/meltblown/spunbond laminate material (hereinafter "SMS"). The SMS material had a basis weight of about 27 grams per square meter. The vapor-permeable barrier layer consisted of a polyolefin film which had a thickness of about 0.7 mil. and a basis weight of about 19.5 grams per square meter. The polyolefin film material was commercially available from Exxon Chemical Patents Incorporated, under the tradename EXXAIRE. The vapor-permeable barrier layer was adhered to the SMS laminate and positioned between the absorbent core and the SMS laminate material of the backsheet. The backsheet had a water vapor transmission rate of about 1500 grams per square meter per 24 hours. The absorbent core was sandwiched between the backsheet and a topsheet composed of a spunbond web of polypropylene fibers having a basis weight of about 17 grams per square meter. A surge management layer composed of a bonded carded web was located between the topsheet and the absorbent core. The surge layer included bicomponent fibers and defined an overall basis weight of about 83 grams per square meter. The surge layer was a homogeneous blend composed of about 60 weight percent polyethylene/polyester (PE/PET), sheath-core bicomponent fibers which had a fiber denier of about 3 d and about 40 weight percent single component polyester fibers which had a fiber denier of about 6 d and which have fiber lengths of from about 3.8 to about 5.08 centimeters. The surge layer further defined a width of about 10.2 centimeters and a length of about 16.5 centimeters. The front edge of the surge layer was located 5.1 centimeters from the front edge of the absorbent core.

The Supreme diapers further included a single component elasticized waistband and waist flap assembly at each longitudinal end of the diaper. The assembly had multiple strands of elastomeric material sandwiched and laminated between a polymer film layer and a nonwoven fabric layer. The polymer film was a 0.00075 inch thick film composed of a blend of a linear low density polyethylene and an ultra low density polyethylene. The nonwoven fabric layer was composed of a 20 grams per square meter web of polypropylene spunbond. The elastic strands were composed of about 8–16 strands of LYCRA® elastomer aligned along the cross-direction of the diaper to elasticize and gather the diaper waistbands and the internal waist flaps. The Supreme diapers also included length-wise containment flaps which extend the full length of the diaper and elasticized leg bands along each longitudinal side edge of the diaper. The elastic strands in the leg band and containment flaps were composed of LYCRA® elastomer aligned along the longitudinal length of the diaper to elasticize and gather the diaper legbands and the containment flaps.

Four samples of the diapers were subjected to the Tracer Gas Test set forth above. The results are set forth in Table 1 below.

TABLE 1

|  | Mean Dry Air Exc. Rate (cm³/min.) | Mean Wet Air Exc. Rate (cm³/min.) | Wet/Dry Ratio |
| --- | --- | --- | --- |
| Example 1 | 822 | 224 | 0.27 |
| Example 2 | 794 | 310 | 0.39 |
| Example 3 | 679 | 220 | 0.32 |
| Example 4 | 1050 | 360 | 0.34 |
| Example 5 | 758 | 190 | 0.25 |
| Example 6 | 724 | 240 | 0.33 |
| Example 7 | 677 | 153 | 0.23 |
| Example 8 | 495 | 316 | 0.63 |
| Comparative Ex. 1 | 51 | 110 | 2.16 |
| Comparative Ex. 2 | 513 | 171 | 0.33 |

The test results from Examples 1–8 and Comparative Examples 1 and 2 indicate that diapers made according to the present invention generally have improved levels of air exchange both when dry and when wet when compared to conventional diapers.

Example 9

Four samples of diapers having the same general construction as the diapers described in connection with Example 2 were hand made and tested according to the Skin Hydration Test set forth above. The diapers were substantially the same as the Example 2 diapers except that the diapers were similar in size to commercially available Step 4 size diapers, the absorbent body was a single layer having the same thickness throughout, and the apertures had a diameter of 2.54 centimeters. The diapers defined an average Skin Hydration Value of 8.1 grams per square meter per hour. The results are also set forth in Table 2 below.

Example 10

Four samples of diapers having the same general construction as the diapers described in connection with Example 6 were hand made and tested according to the Skin Hydration Test set forth above. The diapers were substantially the same as the Example 6 diapers except that the diapers were similar in size to commercially available Step 4 size diapers, the absorbent body defined a basis weight of about 560 grams per square meter and the apertures had a diameter of 2.54 centimeters. The diapers defined an average Skin Hydration Value of 2.8 grams per square meter per hour. The results are also set forth in Table 2 below.

Example 11

Four samples of diapers having the same general construction as the diapers described in connection with Example 7 were hand made and tested according to the Skin Hydration Test set forth above. The diapers were substantially the same as the Example 7 diapers except that the diapers were similar in size to commercially available Step 4 size diapers. The diapers defined an average Skin Hydration Value of 1.6 grams per square meter per hour. The results are also set forth in Table 2 below.

Comparative Example 3

Disposable diapers having the same general construction as those diapers commercially available from Kimberly-Clark Corporation under the trade designation HUGGIES® Supreme Step 4 were tested. In essence, the Step 4 sized Supreme diapers were similar to the Step 3 sized Supreme diapers described above in connection with Comparative Example 2 except that the size of the materials was greater.

Four samples of the diapers were subjected to the Skin Hydration Test set forth above. The diapers defined an average Skin Hydration Value of 19.3 grams per square meter per hour. The results are also set forth in Table 2 below.

TABLE 2

|  | Skin Hydration Value (g/m²/hr) |
| --- | --- |
| Example 9 | 8.1 |
| Example 10 | 2.8 |
| Example 11 | 1.6 |
| Comparative Ex. 3 | 19.3 |

The test results from Examples 9–11 and Comparative Example 3 indicate that diapers made according to the teachings of the present invention exhibit significantly improved Skin Hydration Values when compared to conventional diapers. Specifically, diapers made according to the present invention exhibited a 58 to 92 percent reduction in the Skin Hydration Value. While some reduction in the Skin Hydration Value was anticipated due to the increased amount of air exchange within the diapers, the magnitude of the reduction was unexpected.

Example 12

Samples of diapers having the same general construction as the diapers described in connection with Comparative Example 2 were hand. made and tested. The diapers were substantially the same as the Comparative Example 2 diapers except that the backsheet was modified to define a water vapor transmission rate of about 3000 grams per square meter per 24 hours. The diapers were subjected to the *C. albicans* Viability Test set forth above. The samples of Example 12 and Comparative Example 4 (control) were tested on the volar forearms of each of seven test subjects. Approximately 0.01 milliliters of a 0.9 weight percent saline solution containing a suspension of 5.71 log of *C. albicans* colony forming units was delivered to the test site with micropipettes and the suspension was then spread uniformly across the test site. The sample diapers according to this example defined a mean *C. albicans* viability of 1.96 log of *C. albicans* colony forming units. Accordingly, compared to the mean *C. albicans* viability of the control (Comparative Example 4), the diapers according to this example defined a reduction in the *C. albicans* viability value of 26 percent.

Example 13

Samples of diapers having the same general construction as the diapers described in connection with Example 2 except that the backsheet defines a water vapor transmission rate of about 5000 grams per square meter per 24 hours are made. The diapers are subjected to the *C. albicans* Viability Test set forth above. The samples of Example 13 and Comparative Example 4 (control) are tested on the volar forearms of each of seven test subjects. Approximately 0.01 milliliters of a 0.9 weight percent saline solution containing a suspension of 5.71 log of *C. albicans* colony forming units is delivered to the test site with micropipettes and the suspension is then spread uniformly across the test site. It is anticipated that the sample diapers according to this example would define a mean *C. albicans* viability of more likely less than 1.75 and likely less than 1.50 log of *C. albicans* colony forming units. Accordingly, compared to the mean *C. albicans* viability of the control (Comparative Example 4), it is anticipated that the diapers according to this example will define a reduction in the *C. albicans* viability value of more likely about 34 percent and likely about 43 percent.

Comparative Example 4

Samples of diapers having the same general construction as the diapers described in connection with Comparative Example 2 were hand made and tested. The diapers were substantially the same as the Comparative Example 2 diapers except the backsheet was replaced with a 1.0 mil thick polyethylene film material having a water vapor transmission rate of less than 100 grams per square meter per 24 hours. The diapers were subjected to the *C. albicans* Viability Test set forth above on the volar forearms of each of seven test subjects. Approximately 0.01 milliliters of a 0.9 weight percent saline solution containing a suspension of 5.71 log of *C. albicans* colony forming units was delivered to the test site with micropipettes and the suspension was then spread uniformly across the test site. The sample diapers according to this example defined a mean *C. albicans* viability of 2.65 log of *C. albicans* colony forming units.

Example 14

Samples of diapers having the same general construction as the diapers described in connection with Example 13 were machine made and tested. In particular, the backsheet of the diapers defined a water vapor transmission rate of about 5000 grams per square meter per 24 hours. The diapers were subjected to the *C. albicans* Viability Test set forth above. The samples of Example 14 and Comparative Example 5 (control) were tested on the volar forearms of each of twenty test subjects. Approximately 0.01 milliliters of a 0.9 weight percent saline solution containing a suspension of 4.92 log of *C. albicans* colony forming units was delivered to the test site with micropipettes and the suspension was then spread uniformly across the test site. The sample diapers according to this example defined a mean *C. albicans* viability of 1.26 log of *C. albicans* colony forming units. Accordingly, compared to the mean *C. albicans* viability of the control (Comparative Example 5), the diapers according to this example defined a reduction in the *C. albicans* viability value of 61 percent.

Comparative Example 5

Samples of diapers having the same general construction as the diapers described in connection with Comparative Example 4 were machine made and tested. In particular, the backsheet of the diapers included a 1.0 mil thick polyethylene film material having a water vapor transmission rate of less than 100 grams per square meter per 24 hours. The diapers were subjected to the *C. albicans* Viability Test set forth above on the volar forearms of each of twenty test subjects. Approximately 0.01 milliliters of a 0.9 weight percent saline solution containing a suspension of 4.92 log of *C. albicans* colony forming units was delivered to the test site with micropipettes and the suspension was then spread uniformly across the test site. The sample diapers according to this example defined a mean *C. albicans* viability of 3.26 log of *C. albicans* colony forming units.

The test results from Examples 12 and 14 and the expected results from Example 13 show that diapers made according to the present invention exhibit a reduced viability and incidence of microbial infection when compared to conventional absorbent diapers and the test results from Comparative Examples 4 and 5. It is clear that such reduced microbial viability is achieved by reducing the occlusion of the skin by increasing the breathability of the diaper both when dry and when wet.

Example 15

Figure 7:
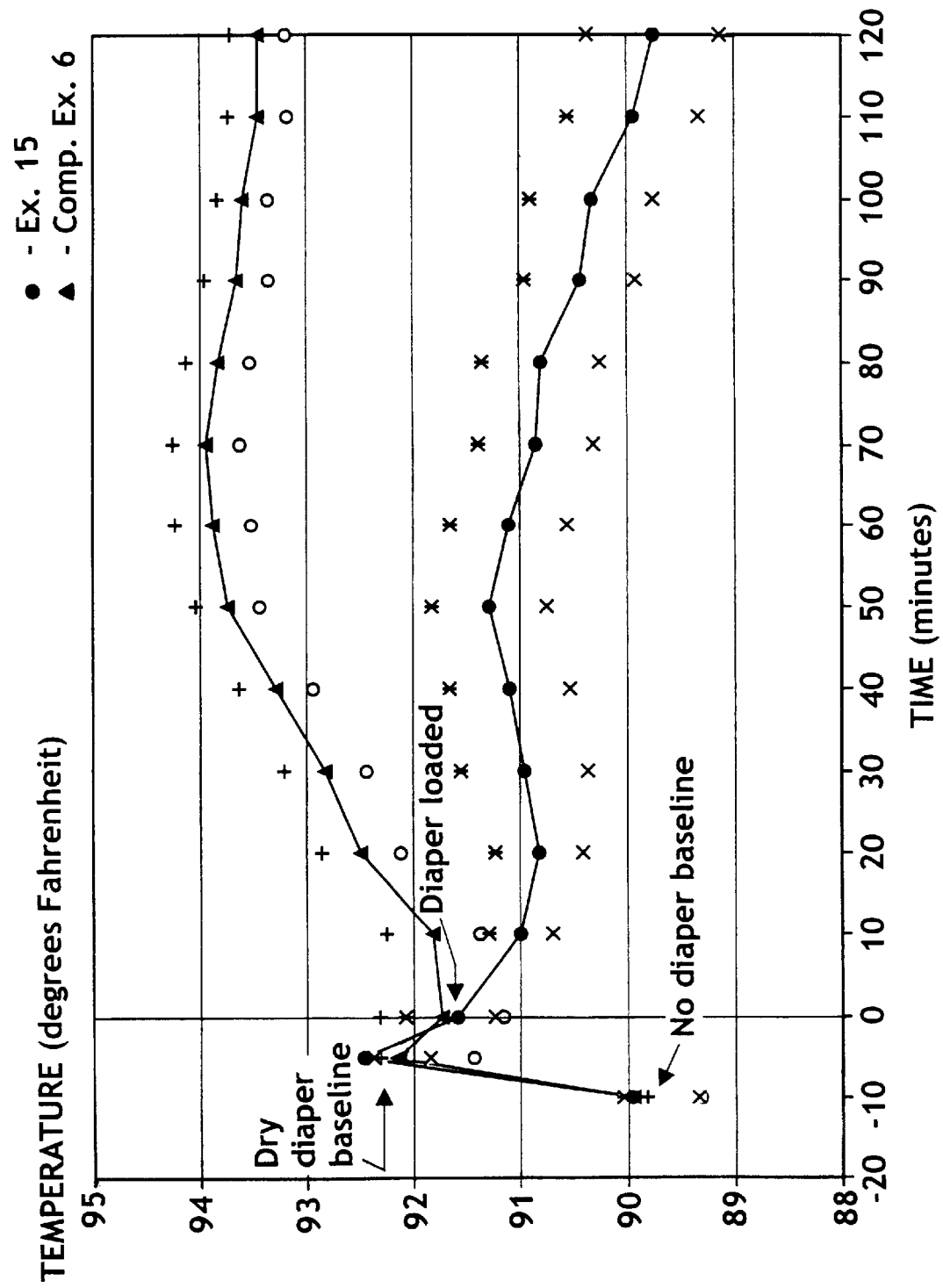
FIG. 7 representatively shows a graph of the data from Example 15 and Comparative Example 6.

Samples of diapers having the same general construction as the diapers described in connection with Example 2 except that the backsheet defined a water vapor transmission rate of about 5000 grams per square meter per 24 hours were made. The diapers were subjected to the Skin Temperature Test set forth above. The samples were tested on one of the forearms of each of eleven test subjects. The results of the test are shown in FIG. 7. The sample diapers according to this example defined a Wet Skin Temperature/Dry Skin Temperature ratio of 0.970.

Comparative Example 6

Samples of diapers having the same general construction as the diapers described in connection with Comparative Example 2 were made. The diapers were substantially the same as the Comparative Example 2 diapers except the backsheet was replaced with a 1.0 mil thick polyethylene film material having a water vapor transmission rate of less than 100 grams per square meter per 24 hours. The diapers were subjected to the Skin Temperature Test set forth above. The samples were tested on one of the forearms of each of eleven test subjects. The results of the test are shown in FIG. 7. The sample diapers according to this example defined a Wet Skin Temperature/Dry Skin Temperature ratio of 1.014.

The test results from Example 15 as shown in FIG. 7 show that diapers made according to the present invention are capable of maintaining a more constant, reduced skin temperature when wet when compared to conventional absorbent diapers and the test results from Comparative Example 6. It is hypothesized that the more constant, reduced skin temperature is achieved by reducing the occlusion of the skin by increasing the breathability of the diaper when wet. Moreover, as shown in FIG. 7, diapers made according to the present invention are capable of maintaining a skin temperature when wet which is substantially the same as the wearer's undiapered skin temperature. Such a maintained skin temperature can result in improved comfort to the wearer.

Example 16

A lotion formulation was prepared having the following composition:

| Ingredient | Weight Percent |
| --- | --- |
| Petrolatum | 55.00 |
| Ozokerite MP 145/155 F | 24.80 |
| Paraffin MP 130/135 F | 4.50 |
| Microcrystalline wax W-835 | 4.50 |
| Cetyl esters (synthetic spermaceti wax) | 4.50 |
| Elvax 410 | 6.70 |

The lotion formulation was prepared by heating the petrolatum to 75° C. and adding the remaining ingredients while maintaining the temperature at 75° C. and mixing until all ingredients were melted and uniform. The lotion formulation defined a bulk melting point of about 45° C. and a melt point viscosity at 60° C. of about 149 centipoise. The melt point viscosity at 45° C. was beyond measuring limits.

The lotion formulation was applied to the topsheet of diapers substantially identical to HUGGIES® Supreme diapers commercially available from Kimberly-Clark Corporation at an add-on rate of about 0.2 grams per diaper. The lotion was applied to the topsheet as a series of 4 lines down the center of the diaper. Each line of lotion had a width of 0.25 inches with a space having a width of 0.75 inches between each line.

The diapers were subjected to the Z-direction Lotion Migration Test whereby five diapers were stored at a temperature of 73° F. for 28 days and five diapers were stored at a temperature of 130° F. for 28 days. The diapers defined a z-direction migration loss of 44.3%. The diapers were also subjected to the CD-direction Lotion Migration Test whereby five diapers were stored at a temperature of 73° F. for 28 days and five diapers were stored at a temperature of 130° F. for 28 days. The diapers defined a cd-direction migration loss of 16.7%.

Comparative Example 7

Samples of PAMPERS® Premium diapers commercially available from The Procter & Gamble Company were obtained. The diapers included a lotion formulation on the topsheet which had the following composition:

| Ingredient | Weight Percent |
| --- | --- |
| Petrolatum | 58.50 |
| Stearyl Alcohol | 41.50 |
| Aloe | trace |

The lotion formulations defined a bulk melting point of about 52°, a melt point viscosity at 50° C. of about 10 centipoise and a melt point viscosity of about 5 centipoise at a temperature of 60° C.

The diapers were subjected to the Z-direction Lotion Migration Test whereby five diapers were stored at a temperature of 73° F. for 28 days and five diapers were stored at a temperature of 130° F. for 28 days. The diapers defined a z-direction migration loss of 62%.

Comparative Example 8

Samples of PAMPERS® Rash Guard diapers commercially available from The Procter & Gamble Company were obtained. The diapers included a lotion formulation on the topsheet which had the following composition:

| Ingredient | Weight Percent |
| --- | --- |
| Petrolatum | 58.50 |
| Stearyl Alcohol | 41.50 |

The lotion formulations defined a bulk melting point of about 52°, a melt point viscosity at 50° C. of about 10 centipoise and a melt point viscosity of about 5 centipoise at a temperature of 60° C.

The diapers were subjected to the Z-direction Lotion Migration Test whereby five diapers were stored at a temperature of 73° F. for 28 days and five diapers were stored at a temperature of 130° F. for 28 days. The diapers defined a z-direction migration loss of 66%.

Comparative Example 9

A lotion formulation was prepared having the following composition:

| Ingredient | Weight Percent |
| --- | --- |
| Petrolatum | 80.00 |
| Stearyl Alcohol | 20.00 |

The lotion formulation was prepared by heating the petrolatum to 75° C. and adding the stearyl alcohol while maintaining the temperature at 75° C. and mixing until all ingredients were melted and uniform. The lotion formulation defined a bulk melting point of about 52° C. and a melt point viscosity at 60° C. of about 5 centipoise.

The lotion formulation was applied to the topsheet of diapers substantially identical to HUGGIES® Supreme diapers commercially available from Kimberly-Clark Corporation at an add-on rate of about 0.2 grams per diaper. The lotion was applied to the topsheet as a series of 4 lines down the center of the diaper. Each line of lotion had a width of 0.25 inches with a space having a width of 0.75 inches between each line.

The diapers were subjected to the Z-direction Lotion Migration Test whereby five diapers were stored at a temperature of 73° F. for 28 days and five diapers were stored at a temperature of 130° F. for 28 days. The diapers defined a z-direction migration loss of 91.7%. The diapers were also subjected to the CD-direction Lotion Migration Test whereby five diapers were stored at a temperature of 73° F. for 28 days and five diapers were stored at a temperature of 130° F. for 28 days. The diapers defined a cd-direction migration loss of 48.9%.

Comparative Example 10

A lotion formulation was prepared having the following composition:

| Ingredient | Weight Percent |
| --- | --- |
| Petrolatum | 52.00 |
| Polyphenylmethyl-siloxane | 20.00 |
| Paraffin Wax | 15.00 |
| Cetearyl Alcohol | 10.00 |
| PEG 2000 | 3.00 |

The lotion formulation was substantially identical to that described in Example 6 in U.S. Pat. No. 5,643,588 issued Jul. 1, 1997 to Roe et al. The lotion formulation was prepared by heating the petrolatum to 75° C., adding the remaining ingredients while maintaining the temperature at 75° C. and mixing until all ingredients were melted and uniform. The lotion formulation defined a bulk melting point of about 54° C. and a melt point viscosity at 60° C. of about 54 centipoise.

The lotion formulation was applied to the topsheet of diapers substantially identical to HUGGIES® Supreme diapers commercially available from Kimberly-Clark Corporation at an add-on rate of about 0.2 grams per diaper. The lotion was applied to the topsheet as a series of 4 lines down the center of the diaper. Each line of lotion had a width of 0.25 inches with a space having a width of 0.75 inches between each line.

The diapers were subjected to the Z-direction Lotion Migration Test whereby five diapers were stored at a temperature of 73° F. for 28 days and five diapers were stored at a temperature of 130° F. for 28 days. The diapers defined a z-direction migration loss of 69.6%. The diapers were also subjected to the CD-direction Lotion Migration Test whereby five diapers were stored at a temperature of 73° F. for 28 days and five diapers were stored at a temperature of 130° F. for 28 days. The diapers defined a cd-direction migration loss of 50.0%.

As representatively shown, the lotion formulations on the absorbent articles of the different aspects of the present invention (Example 16) migrate significantly less than conventional lotion formulations such as those of Comparative Examples 7–10 at elevated temperatures. In particular, the articles of Example 16 exhibited about 50% less z-directional lotion migration and over 60% less cd-directional lotion migration compared to the diapers in Comparative Examples 7–10. Such reduced level of migration at elevated temperatures results in more of the lotion remaining on the bodyfacing surface of the article which can lead to a higher percentage of the lotion transferring to the skin of the wearer to improve skin health and reduce friction.

Examples 17–19

The effect of the treatment compositions of the present invention to inhibit the hydrolysis of a model protein substrate by urine and a fecal extract was determined. In addition, the ability of the treatment compositions to reduce a fecal extract-elicited pro-inflammatory response in EpiDerm™ was measured. The treatment composition applied to a material was placed on the EpiDerm™ sample, both before and after application of the fecal irritant. The release of a pro-inflammatory signaling molecule lnterleukin-1 alpha, was compared to that of the control not containing the treatment composition.

Example 17

Aqueous zinc salts were shown to inhibit a chemical reaction that contributes to diaper rash. The proteolytic activity of fecal extract was measured using fluorescently labeled casein. Inhibiting emulsions of zinc sulfate heptahydrate in water were prepared ranging from 0–1 mM.

A fecal extract sample was prepared from feces obtained from an infant on antibiotics (Sulfatrim) who had diaper rash. To prepare the extract, the feces was suspended in water and vigorously vortexed. After vortexing, the sample was held on ice prior to centrifugation at 15,000 times the force of gravity for 20 minutes. The supernatant was filtered through 0.22 micron cellulose acetate filters and stored at −80° C. until use. Trypsin (molecular weight=23,500 daltons), a protease known to contribute to diaper rash, was measured in the fecal extract at a concentration of 5,850 picomoles/milliliter. Pancreatic elastase (molecular weight=25,000 daltons), a suspected contributor, was measured in the fecal extract at a concentration of 83.6 picomoles/milliliter. The fecal extract (7.1 mg/ml in water) was diluted in water to 2 $\mu$g/ml.

The zinc sulfate heptahydrate (Aldrich Chemicals, Wis.) emulsions (20 $\mu$L) having a molecular weight of 287.5 were added to wells of a 96 white plate (Dynex, Chantilly, Va.) containing 100 $\mu$L of a fecal extract and allowed to incubate for 15 minutes at room temperature. The reaction was initiated with the addition of 80 $\mu$L of 12.5 $\mu$g/ml solution of a fluorescent dye-labeled casein substrate (EnzChek Protease Assay Kit (E-6639), Molecular Probes, Eugene, Oreg.) in 20 mM Tris-HCl, pH 8.0. Reaction of the fecal extract with the casein substrate cleaves the fluorescent dye from the substrate. Relative fluorescence units (RFUs) were collected using the Fluoroskan Ascent System (Labsystems, Incorporated, Needham Heights, Mass.) with excitation and emission filters of 485 and 538 nm, respectively. Data were collected each minute for 15 minutes and rates (RFU/min) were calculated. Using the uninhibited wells as 100% protease activity, percent of fecal proteolytic activity remaining was determined for each concentration of zinc inhibitor (Inhibited Rate/Uninhibited rate* 100).

Figure 9:
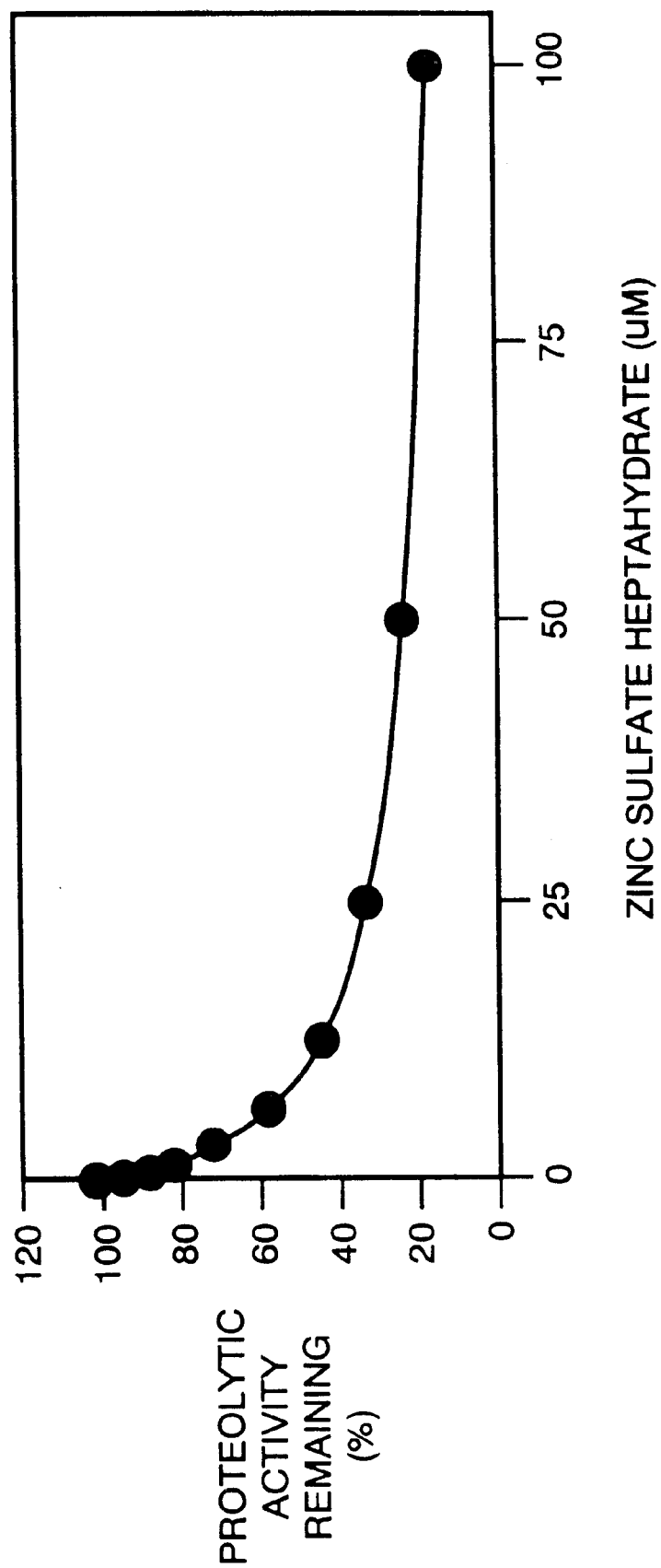
FIGS. 9–13 representatively show the results from Examples 17–21.

The data show that zinc effectively inhibited the hydrolysis of casein by the fecal extract in a dose-dependent manner. A plot of the data for the fecal extract sample is shown in FIG. 9, which is a graph showing how the proteolytic activity of the fecal extract was reduced as the zinc sulfate heptahydrate concentration was increased. These data show that the aqueous zinc emulsion has the ability to neutralize proteases in feces that have been implicated to induce skin inflammation in the diaper environment (Anderson, P. H., Bucher, A. P., Saees, I., Lee, P. C., Davis, J. A., and Maibach, H. I. Faecal enzymes: in vivo skin irritation. *Contact Dermatitis* 1994; 30, 152–158).

Example 18

Aqueous zinc salts were shown to inhibit a chemical reaction that contributes to diaper rash. The proteolytic activity of infant urine was measured using fluorescently-labeled casein. Inhibiting emulsions of zinc sulfate heptahydrate in water were prepared ranging from 0–50 mM.

Two (2) infant urine (100 µL) samples were added to wells of a 96 white plate (Dynex) containing 80 µL of 12.5 µg/ml solution of a fluorescent dye-labeled casein substrate (EnzChek Protease Assay Kit (E-6639)) in 100 mM Tris-HCl, pH 8.0, and allowed to incubate for 60 minutes at 37° C. After the incubation time, 20 µL of zinc sulfate heptahydrate in water, ranging from 0–50 mM was added to the wells. Reaction of the infant urine with the casein substrate cleaves the fluorescent dye from the substrate. RFUs were collected using the Fluoroskan Ascent System with excitation and emission filters of 485 and 538 nm, respectively. Data were collected each minute for 60 minutes at 37° C. and rates (RFU/min) from 30–50 minutes were calculated for each zinc concentration. Using the uninhibited wells as 100% protease activity, percent of urine proteolytic activity remaining was determined for each concentration of zinc inhibitor (Inhibited Rate/Uninhibited rate* 100).

Figure 10:
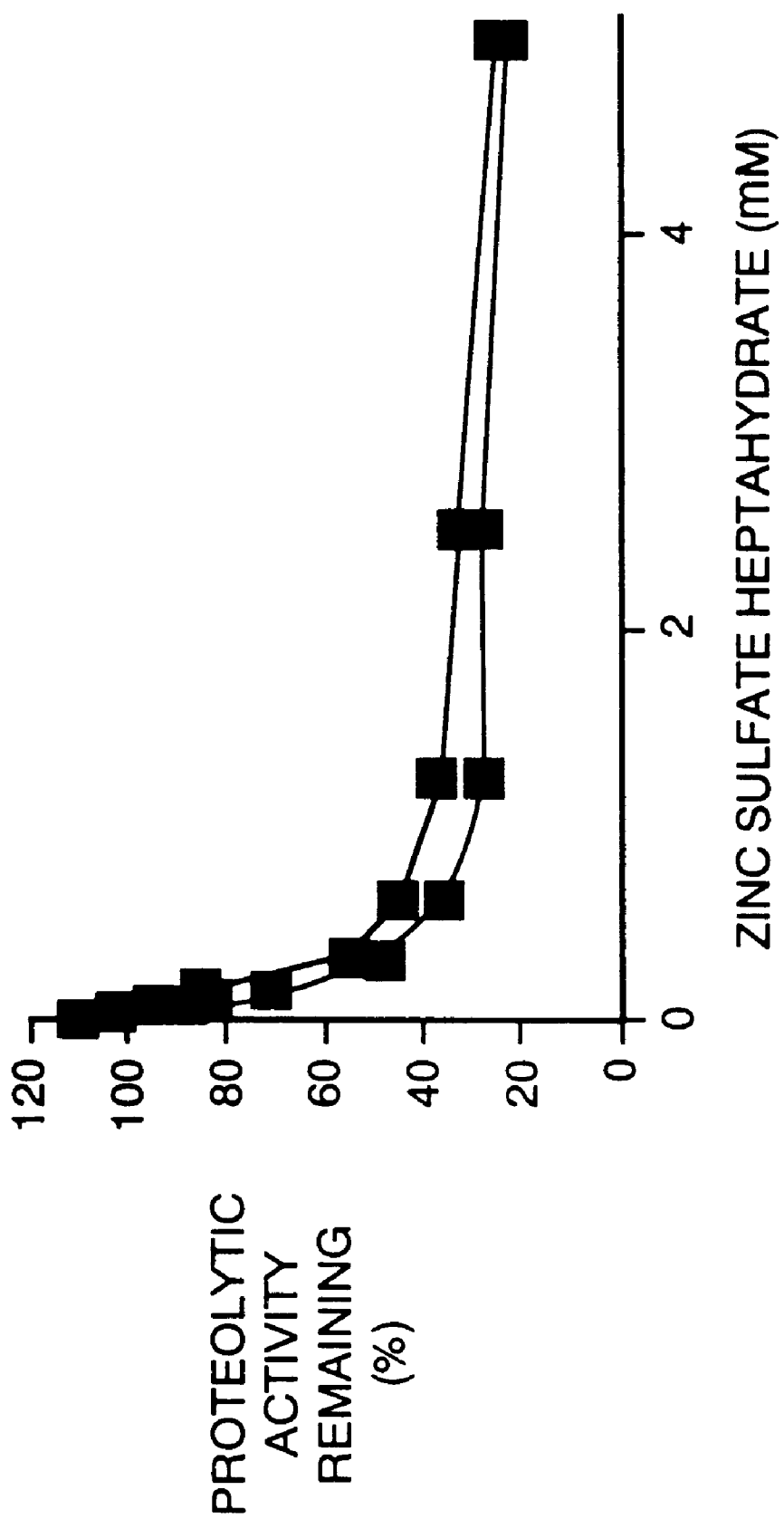

The data show that zinc effectively inhibited the hydrolysis of casein by infant urine in a dose-dependent manner. A plot of the data is shown in FIG. 10, which is a graph showing how the proteolytic activity of infant urine was reduced as the zinc sulfate heptahydrate concentration was increased. These data show that the aqueous zinc emulsion has the ability to neutralize proteases in infant urine.

Example 19

Zinc sulfate heptahydrate was also shown to inhibit the reaction of fecal extract with synthetic skin. The synthetic skin, EpiDerm™ 201 (MatTek Corporation, Ashland, Mass.) contains keratinocytes that release interleukin-1 alpha (IL-1 alpha) when subjected to proteases in the fecal extract. When the IL-1 alpha was released, it diffused from the skin into the fluid below the EpiDerm™. Samples of this fluid were taken and analyzed for the presence of the IL-1 alpha. Higher levels of IL-1 alpha was indicative of greater skin irritation.

Prior to application onto the EpiDerm™, the fecal extract (10.4 µL) was pre-incubated for 30 minutes at room temperature with 250 mM zinc sulfate heptahydrate in water (2.6 µL). Water only and fecal extract only samples served as controls. After application of the samples to the EpiDerm™, 25 µL aliquots were removed from the underlying media at 8, 12, and 24 hours to test for the presence of the IL-1 alpha. The aliquots were directly added to a 1.5 mL micro-centrifuge tube containing 225 µL of filtered-sterilized 20 mM Tris-HCl, pH 8.0, 1% BSA buffer and stored at −80° C. After all samples were collected, IL-1 alpha levels were quantified using the R&D Systems Interleukin-1 alpha Quantikine Kit (R&D Systems, Minneapolis, Minn.).

Figure 11:
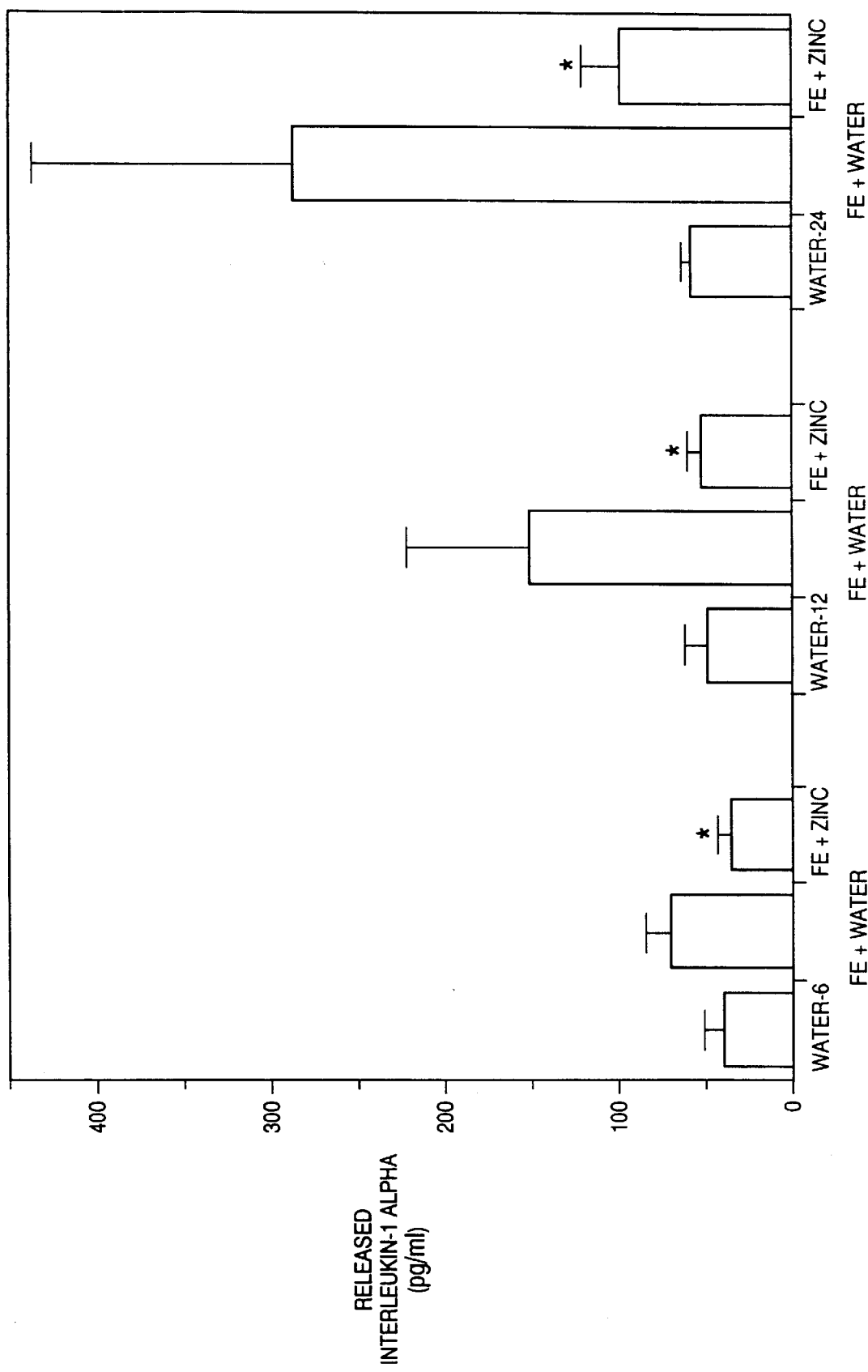

A plot of the data is shown in FIG. 11, which is a graph showing that the addition of the zinc sulfate heptahydrate (FE+zinc) reduced the amount of interleukin-1 alpha released into the underlying media relative to the application of the substrate treated with uninhibited fecal extract (FE +water). A similar reduction was shown at 8, 12, and 24 hours. The asterisk over the error bars in FIG. 11 represent a Student t-test 95% confidence interval.

Figure 12:
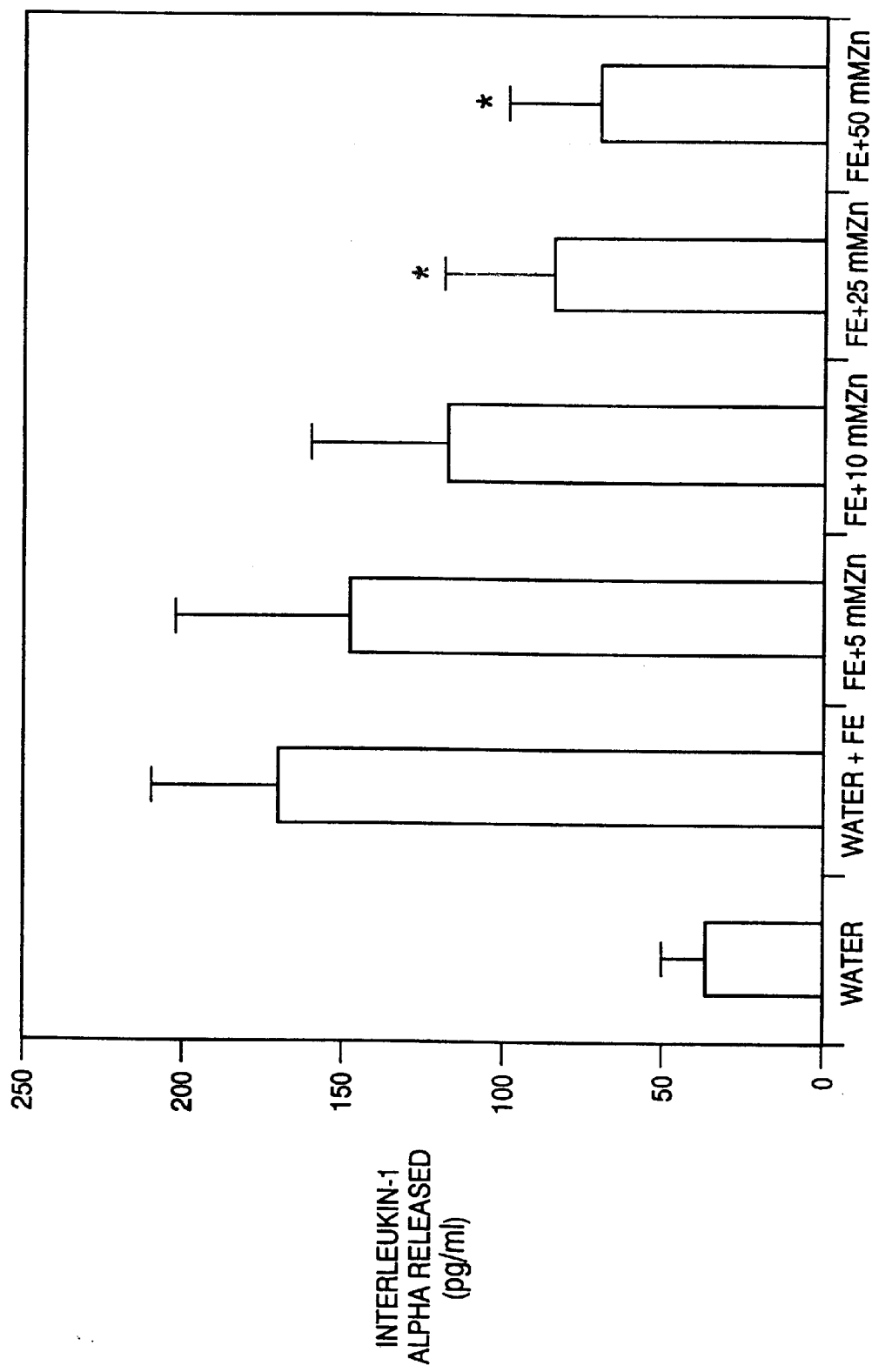

Re-running the same experiment with varied concentrations of zinc sulfate heptahydrate (0, 25, 50, 125, and 250 mM) in the 2.6 µL aliquot added to the 10.4 µL sample of fecal extract, demonstrated that zinc sulfate heptahydrate effectively inhibits the proteolytic activity of fecal extract in a dose-dependent manner. A plot of the data, shown in FIG. 12, shows that the proteolytic activity of fecal extract is reduced as the zinc sulfate heptahydrate concentration is increased.

Example 20

Skin treatment compositions of the present invention were formed by creating an emulsion (or microemulsion) of a skin health benefit agent and water as the carrier liquid. Aqueous emulsions of zinc salt as the skin health benefit agent, AHCOVEL, as the surfactant system, and CROSILK as the silk protein, were prepared. The stable emulsions were diluted to about a 5% by weight emulsion and applied to the surface of a polyolefin nonwoven topsheet fabric via a saturation dip and squeeze process as follows:

Untreated polypropylene spunbond materials (basis weight of about 0.5 ounces per square yard) were used as a substrate for the treatment compositions. The compositions were applied to the substrates by a low-solids batch treatment process. An 8 in.×12 in. (20.32×30.48 cm) example of the substrate was first dipped in an aqueous treatment bath of known composition illustrated in Table 3 below.

TABLE 3

Treatment Bath Concentration

| Example | Composition | Water | Ahcovel Base N-62 | Crosilk 10,000 | Zinc Sulfate Monohydrate |
|---------|-------------|-------|-------------------|----------------|--------------------------|
| 1 | Control | 98.8 | 1.2 | — | — |
| 2 | 1 | 98.148 | 1.2 | .6 | .054 |

The saturated examples were then nipped between two rubber rollers in a laboratory wringer, Type LW-1, No. LW-83A (Atlas Electric Devices, Chicago, Ill.), and subsequently dried in an oven at 60° C. for about 20 minutes or until constant weight was obtained. Nip pressure was adjusted to achieve a 100% wet pick-up (%WPU). %WPU is calculated from the following equation:

%WPU=[(Ww−Wd)/Wd]×100, where:

Ww=wet weight of the nipped fabric,

Wd=dry weight of the treated fabric.

Knowing the bath concentration and the %WPU, the % Add On can be calculated from the following equation:

%AddOn=(%BathConcentration)×(%WPu)÷100

If, as in this example, the %WPU=100, then the % Add-On will equal the % Bath Concentration. However, other %WPU and % Bath Concentration combinations can be used to achieve similar results.

The treated spunbond materials were tested to assess their capacity to inhibit the reaction of fecal extract with synthetic skin. The fecal extract was prepared from feces obtained from an infant on antibiotics (Sulfatrim) who had diaper rash. To prepare the extract, the feces were suspended in water and vigorously vortexed. After vortexing, the samples were held on ice prior to centrifugation at 15,000 times the force of gravity for 20 minutes. The supernatant was filtered through 0.22 micron cellulose acetate filters and stored at −70° C. until use. Trypsin (molecular weight=23,500 daltons), a protease known to contribute to diaper rash, was measured in the fecal extract at a concentration of 5,850 picomoles/milliliter. Pancreatic elastase (molecular weight=

25,000 daltons), a suspected contributor, was measured in the fecal extract at a concentration of 83.6 picomoles/milliliter.

The synthetic skin, EpiDerm™ 201 (MatTek Corporation, Ashland, Mass.) contains keratinocytes that release interleukin-1 alpha (IL-1 alpha) when subjected to proteases such as trypsin and pancreatic elastase. When the IL-1 alpha is released, it diffuses from the skin into the fluid below the EpiDerm™. Samples of this fluid are taken and analyzed for the presence of the IL-1 alpha. Higher levels of IL-1 alpha are indicative of greater skin irritation.

To perform the experiment, 10 μL of water was applied to the surface of the synthetic skin. The treated spunbond materials were cut into about 0.9 cm discs which were placed on top of the water on the EpiDerm™. After about a two hour incubation at 37° C., the discs were removed and the EpiDerm™ was insulted with 15 μL of insult fluid where each of the treated spunbond discs had been. A second treated spunbond disc was then placed on top of the insult fluid to simulate the diaper environment. After 11 hours at 37° C., an aliquot from the underlying fluid bathing the EpiDerm™ was removed and the amount of IL-1 alpha quantified using the R&D Systems Interleukin-1 alpha Quantikine Kit (R&D Systems, Minneapolis, Minn.).

Four treatments were done using the two examples from Table 1 and two insult fluids (fecal extract and water) as shown in Table 4.

TABLE 4

EpiDerm ™ treatments

| Code | Example Used | Insult Fluid |
| --- | --- | --- |
| A | 1 (Control) | Water |
| B | 1 (Control) | Fecal Extract |
| C | 2 | Water |
| D | 2 | Fecal Extract |

The results of the experiments of Table 4 are shown below in Table 5. The application of the materials treated with Crosilk and Zinc (Code C and D) to the EpiDerm™ reduced the amount of interleukin-1 alpha released into the underlying media relative to the application of the materials treated with just Ahcovel (Code A and B, respectively).

TABLE 5

IL-1 alpha Released (picograms/milliliter)

| Code | Mean | Standard Deviation | Number of samples |
| --- | --- | --- | --- |
| A | 14.03 | 4.768 | 6 |
| B | 105 | 66 | 5 |
| C | 6.77 | 6.77 | 6 |
| D | 44.92 | 23.4 | 6 |

Example 21

Water soluble silk protein (SERICIN, Pentapharm AG, Basel, Switzerland) and hydrolyzed silk (CROSILK 10,000, Croda, Incorporated, Parsippany, N.J.) were individually shown to inhibit proteolytic activity in the fecal extract that has been implicated to contribute to diaper rash. Serial dilutions of the neat protein and hydrolysate were performed with 100 mM Tris-HCl pH 8.0 as the diluent. The silk protein concentrations were determined using a Macro BCA Protein Assay Reagent Kit (Pierce, Rockford, Ill.).

Fecal extract was prepared as described above for the examples of silk protein and zinc compositions. SERICIN and CROSILK (20 μL) were added to wells of a 96 white plate (Dynex, Chantilly, Va.) containing 80 μL of a 12.5 μg/ml solution of a fluorescent dye-labeled casein substrate (EnzChek Protease Assay Kit (E-6639), Molecular Probes, Eugene, Oreg.). The reaction was initiated with the addition of 100 μL of the 2 μg/ml fecal extract. Reaction of the fecal extract with the casein substrate cleaves the fluorescent dye from the substrate. Relative fluorescence units (RFUs) were collected using the Fluoroskan Ascent System (Labsystems, Incorporated, Needham Heights, Mass.) with excitation and emission filters of 485 and 538 nm, respectively. The reaction was run for 30 min. at room temperature and rates (RFU/min) from 10–20 minutes were calculated. Percent of fecal proteolytic activity remaining was determined for each concentration of SERICN and CROSILK inhibitor (Inhibited Rate/Uninhibited rate* 100).

Figure 13:
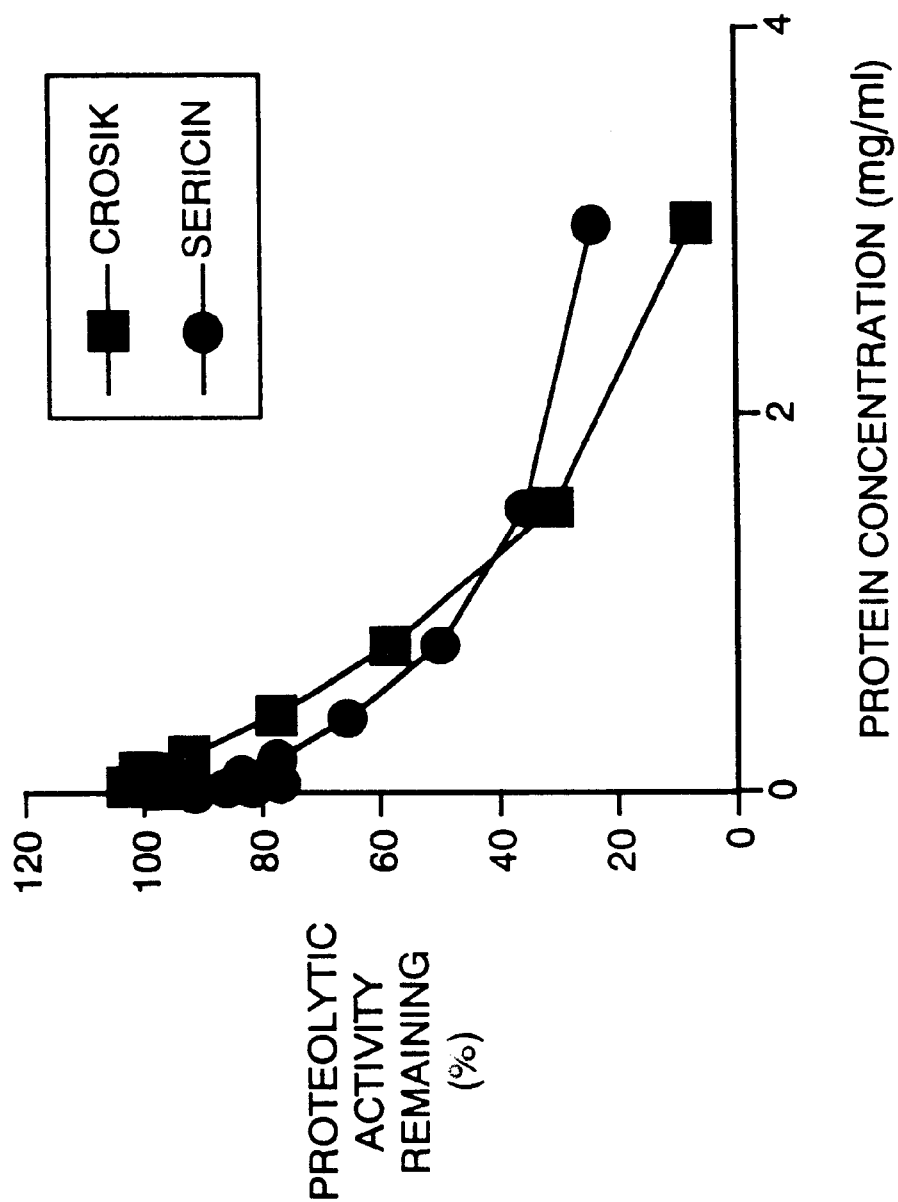

A plot of the data is shown in FIG. 13, which is a graph showing reduction of proteolytic activity with increasing concentrations of both SERICIN and CROSILK. These data suggest that both molecules have the ability to neutralize proteases in feces that have been implicated to induce skin inflammation in the diaper environment (Faecal enzymes: in vivo skin irritation, supra).

As representatively shown in Examples 17–21, the various treatment compositions on the topsheets of absorbent articles of the different aspects of the present invention effectively inhibits the proteolytic activity of fecal extracts when transferred to the skin. Such reduced level of proteolytic activity can result in improved skin health.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. A disposable absorbent article which defines a front waist section, a rear waist section, and an intermediate section which interconnects said front and rear waist sections, said absorbent article comprising:
   a) a vapor permeable backsheet which defines a Water Vapor Transmission Rate of at least about 1000 grams per square meter per 24 hours calculated according to a Water Vapor Transmission Test;
   b) a liquid permeable topsheet which is positioned in facing relation with said backsheet;
   c) an absorbent body located between said backsheet and said topsheet; and
   d) a treatment composition on at least a portion of a bodyfacing surface of said topsheet of said absorbent article which includes:
      i) a surfactant; and
      ii) a skin health benefit agent wherein said treatment composition transfers through dissolution.

2. The absorbent article of claim 1 and further comprising a ventilation layer located between said backsheet and said absorbent body.

3. The absorbent article of claim 2 wherein said ventilation layer comprises a hydrophobic, nonwoven material having a thickness of at least about 0.10 centimeters and a basis weight of from about 20 to about 120 grams per square meter.

4. The absorbent article of claim 1 and further comprising a surge management layer which is located between said topsheet and said absorbent wherein said surge management layer comprises a nonwoven material having a basis weight of from about 30 to about 120 grams per square meter.

5. The absorbent article of claim 1 wherein said Water Vapor Transmission Rate of said vapor permeable backsheet is at least about 1500 grams per square meter per 24 hours calculated according to said Water Vapor Transmission Test.

6. The absorbent article of claim 1 wherein said absorbent body defines zones of high air permeability which define a Frazier Porosity which is at least about 10 percent greater than a Frazier Porosity of portions of said absorbent body adjacent to said zones of high air permeability.

7. The absorbent article of claim 6 wherein said zones of high air permeability comprise from about 5to about 75 percent of a total surface area of said absorbent body.

8. The absorbent article of claim 6 wherein said absorbent body includes a plurality of air passageways therethrough to provide said zones of high air permeability.

9. The absorbent article of claim 1 wherein said surfactant is selected from the group comprising ethoxylated hydrogenated fatty oils, monosaccharides, monosaccharide derivatives, polysaccharides, polysaccharide derivatives and combinations thereof.

10. The absorbent article of claim 1 wherein said skin health benefit agent comprises aqueous zinc salt or zinc sulfate monohydrate.

11. The absorbent article of claim 10 wherein said surfactant and zinc salt form said treatment composition and are present at a weight ratio of about 0.01–25 wt. % zinc salt to about 75–99.99 wt. % surfactant.

12. The absorbent article of claim 1 wherein said skin health benefit agent comprises a protein.

13. The absorbent article of claim 12 wherein said protein comprises a silk protein.

14. The absorbent article of claim 13 wherein said silk protein comprises sericin.

15. The absorbent article of claim 10 wherein said skin health benefit agent further comprises a protein.

16. The absorbent article of claim 1 wherein said treatment composition is applied to said topsheet at a level of about 0.1–1.5% by weight relative to a weight of said topsheet.

17. The absorbent article of claim 1 wherein said absorbent article defines a Wet Air Exchange Rate of at least about 190 cubic centimeters per minute and a Dry Air Exchange Rate of at least about 525 cubic centimeters per minute calculated according to a Tracer Gas Test.

18. The absorbent article of claim 1 wherein said absorbent article defines a Wet Air Exchange Rate/Dry Air Exchange Rate ratio of at least about 0.20 calculated according to a Tracer Gas Test.

19. The absorbent article of claim 1 wherein said absorbent article defines a Skin Hydration Value of less than about 18 grams per square meter per hour calculated according to a Skin Hydration Test.

20. The absorbent article of claim 1 wherein said absorbent article defines a Skin Hydration Value of less than about 15 grams per square meter per hour calculated according to a Skin Hydration Test.

21. The absorbent article of claim 1 wherein said absorbent article defines a Wet Skin Temperature/Dry Skin Temperature Ratio of no more than about 1.010 calculated according to a Skin Temperature Test.

* * * * *